(12) United States Patent
Deterding et al.

(10) Patent No.: US 10,910,106 B2
(45) Date of Patent: Feb. 2, 2021

(54) PERSONALIZED HEALTH CARE WEARABLE SENSOR SYSTEM

(71) Applicant: The Regents of the University of Colorado, a body corporate, Denver, CO (US)

(72) Inventors: Robin Deterding, Boulder, CO (US); Tam Vu, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 15/778,142

(22) PCT Filed: Nov. 23, 2016

(86) PCT No.: PCT/US2016/063601
§ 371 (c)(1),
(2) Date: May 22, 2018

(87) PCT Pub. No.: WO2017/091726
PCT Pub. Date: Jun. 1, 2017

(65) Prior Publication Data
US 2018/0325385 A1 Nov. 15, 2018

Related U.S. Application Data
(60) Provisional application No. 62/258,921, filed on Nov. 23, 2015.

(51) Int. Cl.
*A61B 5/11* (2006.01)
*A61B 5/16* (2006.01)
(Continued)

(52) U.S. Cl.
CPC ............ *G16H 40/67* (2018.01); *A61B 5/002* (2013.01); *A61B 5/0022* (2013.01);
(Continued)

(58) Field of Classification Search
CPC combination set(s) only.
See application file for complete search history.

(56) References Cited

U.S. PATENT DOCUMENTS

2008/0146892 A1   6/2008   LeBoeuf et al.
2011/0092779 A1   4/2011   Chang et al.
(Continued)

OTHER PUBLICATIONS

Corresponding European Patent Application No. 16869270.5; Extended European Search Report, dated Jun. 18, 2019, 10 pages.
(Continued)

*Primary Examiner* — Jon Eric C Morales
(74) *Attorney, Agent, or Firm* — Craig R. Miles; CR Miles P.C.

(57) ABSTRACT

Embodiments of the present technology include a wearable physiological monitoring device, related algorithms and software that are tied to a portable electronic device for readout. The wearable device can perform real-time measurement of a number of physiological and environmental parameters including heart rate, pulse oximetry, respiration, movement, environmental particulate matter, moisture, temperature (e.g., ambient air and body temperatures) and geospatial location. Some embodiments may establish a physiological baseline for a patient by measuring the above parameters during a healthy state. Collected data can be wirelessly transmitted to a portable electronic device or monitoring and feedback platform where software will analyze the data and make assessments of the device wearer's health based upon the wearer's baseline.

11 Claims, 26 Drawing Sheets

(51) Int. Cl.
| | |
|---|---|
| *A61B 5/00* | (2006.01) |
| *A61B 5/02* | (2006.01) |
| *G16H 40/67* | (2018.01) |
| *A61B 5/1455* | (2006.01) |
| *G16H 40/63* | (2018.01) |
| *G16H 50/30* | (2018.01) |
| *G16H 50/20* | (2018.01) |
| *A61B 5/0205* | (2006.01) |
| *A61B 5/08* | (2006.01) |
| *A61B 5/117* | (2016.01) |
| *G06F 1/16* | (2006.01) |
| *A61B 5/024* | (2006.01) |
| *A61B 5/01* | (2006.01) |

(52) U.S. Cl.
CPC .............. *A61B 5/0205* (2013.01); *A61B 5/08* (2013.01); *A61B 5/117* (2013.01); *A61B 5/1123* (2013.01); *A61B 5/14551* (2013.01); *A61B 5/486* (2013.01); *A61B 5/7267* (2013.01); *A61B 5/7282* (2013.01); *G06F 1/163* (2013.01); *G16H 40/63* (2018.01); *G16H 50/20* (2018.01); *G16H 50/30* (2018.01); *A61B 5/01* (2013.01); *A61B 5/02438* (2013.01); *A61B 5/0816* (2013.01); *A61B 5/1112* (2013.01); *A61B 5/6898* (2013.01); *A61B 5/7264* (2013.01); *A61B 5/746* (2013.01); *A61B 5/7465* (2013.01); *A61B 2503/06* (2013.01); *A61B 2560/0242* (2013.01); *A61B 2560/0252* (2013.01); *A61B 2562/029* (2013.01)

(56) References Cited

U.S. PATENT DOCUMENTS

| | | |
|---|---|---|
| 2012/0226771 A1 | 9/2012 | Harrington et al. |
| 2015/0113417 A1 | 4/2015 | Yuen et al. |
| 2015/0201854 A1 | 7/2015 | Hong et al. |
| 2015/0223731 A1 | 8/2015 | Sahin |
| 2015/0282717 A1 | 10/2015 | McCombie et al. |

OTHER PUBLICATIONS

International Application No. PCT/US2016/063601, International Search Report & Written Opinion, 9 pages, dated Feb. 2, 2017.
Messinger et al. Novel pediatric-automated respiratory score using physiologic data and machine learning in asthma. Pediatric Pulmonology, 2019; 54:1149-1155.

FIG. 9

|  | SP02 | Fi02 | HR | PULSE | RESP |
|---|---|---|---|---|---|
| Mean (err.) | 0.01 | 0.0064 | 1.4863 | 1.1542 | 1.1515 |
| Std. (err.) | 0.2721 | 0.2667 | 2.0892 | 2.2224 | 1.6315 |

*FIG. 14*

| | SP02 | FiO2 | HR | PULSE | RESP | PAS | PR_PAS |
|---|---|---|---|---|---|---|---|
| Worst | 100 | 30 | 141 | 140 | 34 | 6 | 10.903 |
| | 100 | 35 | 137 | 135 | 24 | 5 | 5 |
| Near by | 100 | 35 | 148 | 138 | 25 | 5 | 5 |
| | 100 | 35 | 139 | 134 | 21 | 5 | 5 |

*FIG. 18*

|  | 100 | 500 | 1000 |
|---|---|---|---|
| Mean | 0.2263 | 0.37816 | 0.24818 |
| Std. | 0.50196 | 1.9258 | 0.61744 |

*FIG. 22*

PERSONALIZED HEALTH CARE WEARABLE SENSOR SYSTEM

CROSS-REFERENCE TO RELATED APPLICATION

This application claims the benefit of U.S. Provisional Application No. 62/258,921, filed on Nov. 23, 2015, entitled "Personalized Health Care Wearable Sensor System," which is hereby incorporated by reference for all purposes in its entirety.

TECHNICAL FIELD

Various embodiments of the present technology generally relate to personalized health care monitoring systems. More specifically, some embodiments, generally relate to wearable pediatric physiologic monitoring systems to optimize lung disease management and wellness.

BACKGROUND

Healthcare is undergoing a major revolution with advances in technology, healthcare systems and molecular science. People and health care systems are seeking ways to optimize health through more personalized approaches that focus on an individual's unique genes, proteins and data. Consumers in the market and patients want to be perceived as unique individuals and understand how they personally respond to their own medications, fitness, wellness and health. As a result, medical consumers are seeking more customized solutions for medicine and wellness to support personalized health.

Children often have specific health care needs that are uniquely different than adults and could benefit from personalized pediatric devices. For example, children do not or cannot describe their symptoms or seek therapy on their own and are unable to complete standard adult pulmonary function testing which is the gold standard outcome measure in lung disease. They are frequently away from parents in day care or in a school where they are less observed creating significant anxiety for parents. Finally, only about 20% of all drugs used in children have been studied and are FDA approved. Though there are many reasons for this, one major reason in children with breathing-related diseases is the lack of quality outcome measures to understand therapeutic response.

As one example, the respiratory disease burden for children is very high and represents the most common area of illness for children. Asthma is the most common chronic disease of childhood with data to suggest that the incidence is increasing and that around 20% of children are impacted in some way by this disease. Exercise-induced asthma is often under-diagnosed. Cough is also one of the most common reasons for children to see a healthcare provider. Other diseases such as lung disease in premature infants, children with underlying disease like cerebral palsy or Down Syndrome who can have frequent breathing issues, infections in the lung, or rare disease such as Cystic Fibrosis add to the spectrum of pediatric respiratory disease. It is estimated that over 25% of all admissions to the Children's Hospital of Colorado can be associated with a breathing-related problem. Many of these respiratory diseases have significant and potentially life threatening breathing issues that impact healthcare costs and family and child quality of life. It is with respect to these and other issues that various embodiments of the present technology have been developed.

BRIEF DESCRIPTION OF THE DRAWINGS

Embodiments of the present technology will be described and explained through the use of the accompanying drawings in which:

FIG. 9 is an example of a graphical user interface that may be used in accordance with various embodiments of the present technology;

FIG. 14 is an example evaluation of vital data regression model according to one or more embodiments of the present technology;

FIG. 18 is an example table showing outliers of a Fuzzy model-based time stamp window in predictions associated with pediatric asthma score (PAS) according to one or more embodiments of the present technology;

FIG. 22 is an example table showing comparisons of experiments with 100 epochs, 500 epochs, and 1000 epochs in connection with evaluations associated with pediatric asthma score (PAS) according to one or more embodiments of the present technology;

Figure 1:
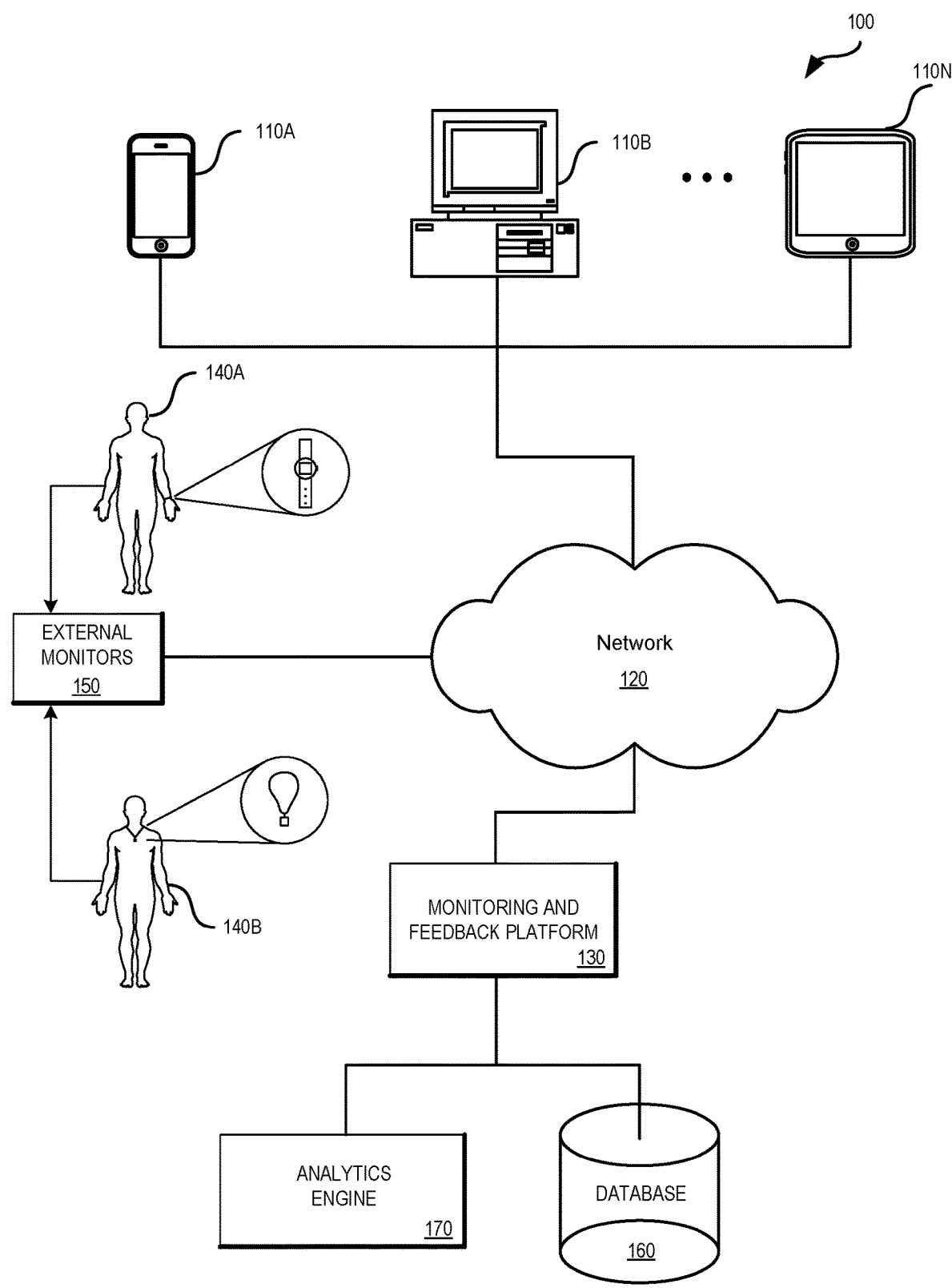
FIG. 1 illustrates an example of a network-based environment in which some embodiments of the present technology may be utilized.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to personalized health care monitoring systems. More specifically, some embodiments, generally relate to wearable pediatric physiologic monitoring systems to optimize lung disease management and wellness. In accordance with some embodiments, pediatric wearable devices can be used to even better define these diseases with the physiologic insights that could be achieved from the monitoring.

Various embodiments provide for wearable devices in children linked to various computer systems and monitoring and feedback platforms capable of running algorithms to automatically analyze physiologic data (e.g., heart rate, respiratory rate, oxygen level, movement, etc.) to predict disease exacerbation and/or response to therapy. Currently, there are no wearable pediatric devices being actively prescribed in pediatric lung disease nor are there algorithms that use a combination of big data variables as outcome variables or as alert devices for parents. There are significant issues that currently produce gaps in success with wearable sensors in the personalized health care market place.

Some embodiments of the present technology use big data sources related to physiological variables and monitoring to create personalized healthcare analysis that has health and wellness applications in both recreation and medical areas. Some embodiments of the present technology include wearable physiological monitoring devices, related algorithms and software that that can be used to generate customized real-time, near real-time, or delayed analysis of patient health. In some embodiments, the wearable device will perform real-time measurement of a number of physiological and/or environmental parameters such as, but not limited to, heart rate, pulse oximetry, respiration, movement, environmental particulate matter, and geospatial location. This data may be wirelessly transmitted to a portable electronic device or monitoring and feedback platform where software will analyze the data and make assessments of the device wearer's health. In some embodiments, the system may be capable of early identification of illness, defining response to therapy, notification of parents and health providers for timely intervention and will ultimately decrease healthcare utilization and improve quality of life for users (e.g., children).

Some embodiments of the present disclosure provide the following advantages: (1) real time or almost real time monitoring of a patient's physiological data separately or in combination with environmental data for an environment in the vicinity of the patient, (2) detection of onset of a pulmonary event for the patient, (3) capabilities of reporting a patient's physiological data and analysis of the physiological data to a medical practitioner, the patient and/or the patient's family, wherein the report provided can vary based on amount of details included in the report, and (4) application of one or more adaptive learning algorithms from machine learning methodologies to detect patterns in the patient's physiological data separately or in combination with environmental data.

In some embodiments, the system may first establish a physiological baseline for a patient by measuring the above parameters during a healthy state. Algorithmic calculation of real time data inputs from a wearable device can identify quantifiable deviations from the baseline and allow determination of health status at any given point in time. If health status deviates (e.g., more than a set percentage or less than a set percentage) from the baseline, an alert will be wirelessly transmitted to portable electronic devices of caregivers.

Depending on the end user, varying information may be displayed on the reporting device, e.g., the caregiver's device. For the at-home user, a parent may see a dashboard indicating the child's health score (1-100) with a Red/Yellow/Green (R/Y/G) indicator. A physician may see a readout of the physiological parameters in addition to the health score and the R/Y/G indicator. The system can be implemented in a number of ways to include usage by parents to monitor children at risk of pulmonary events. The devices can monitor a child's physiology and environmental factors and predict likelihood or detect onset of a pulmonary event. The device could also be used in the clinical setting to identify patients that are experiencing illness, responding (or not responding) to therapy. It could be used to track adherence to medications and track outcome measures for clinical studies.

In the following description, for the purposes of explanation, numerous specific details are set forth in order to provide a thorough understanding of embodiments of the present technology. It will be apparent, however, to one skilled in the art that embodiments of the present technology may be practiced without some of these specific details. While, for convenience, embodiments of the present technology are described with reference to wearable pediatric physiologic monitoring systems to optimize cardiopulmonary disease management and wellness, embodiments of the present technology are equally applicable to various other target audiences and/or disease management.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

FIG. 1 illustrates an example of a network-based environment 100 in which some embodiments of the present technology may be utilized. As illustrated in FIG. 1, environment 100 may include one or more reporting (or monitoring) devices 110A-110N (such as a mobile phone, tablet computer, mobile media device, vehicle-based computer, wearable computing device, clinical device, etc.), communications network 120, monitoring and feedback platform 130, users 140A-140N wearing monitoring devices, external monitors 150, database 160, and analytics engine 170. As described in more detail below, monitoring devices worn by users 140 can monitor a variety of physiological parameters which can be transmitted to monitoring and feedback platform 130 and/or reporting devices 110A-110N for analysis.

In accordance with various embodiments, the wearable monitoring devices worn by users 140 may measure a set of physiological parameters. Such a set of physiological parameters are not currently measured by other systems, including those for monitoring health of adults. Additionally, the wearable monitoring devices can be positioned at one or more locations on the user's body where more accurate readings of the parameters can be obtained relative to currently marketed devices. In some embodiments, sensors coupled to the wearable device are more sensitive and smaller making the wearable device easier and more appealing to wear. In some embodiments, the wearable monitoring devices worn by users 140 may include a compression-type arm sleeve, arm cuff, wrist band, shirt, chest patch, chest band, leg band, and/or the like.

Reporting devices 110A-110N can include network communication components that enable the reporting devices to communicate with monitoring and feedback platform 130 or other portable electronic devices by transmitting and receiving wireless signals using licensed, semi-licensed or unlicensed spectrum over communications network 120. In some cases, communication network 120 may be comprised of multiple networks, even multiple heterogeneous networks, such as one or more border networks, voice networks, broadband networks, service provider networks, Internet Service Provider (ISP) networks, and/or Public Switched Telephone Networks (PSTNs), interconnected via gateways operable to facilitate communications between and among the various networks. Communications network 120 can also include third-party communications networks such as a Global System for Mobile (GSM) mobile communications network, a code/time division multiple access (CDMA/TDMA) mobile communications network, a 3rd or 4th generation (3G/4G) mobile communications network (e.g., General Packet Radio Service (GPRS/EGPRS)), Enhanced Data rates for GSM Evolution (EDGE), Universal Mobile Telecommunications System (UMTS), or Long Term Evolution (LTE) network), or other communications network.

External monitors 150 may include various types of environmental monitors capable of detecting particulate or allergens. This data from the external monitors may be helpful to determine physiologic variance based on a physiologic response. Not only can this data help in detecting abnormal physiologic response but this data can also help in understanding the causes or triggers behind the physiologic response. There could be a wide range of triggers, such as particulate, dander, exercise, etc. In some scenarios, some triggers may be more pertinent to a patient's abnormal psychologic response than others. For example, particulate may not stimulate an abnormal response in some patients, or may not be consistently stimulating abnormal responses in the same patient, or the response caused due to the particulate trigger may be delayed.

Data from the wearable monitoring devices and external monitors 150 may be stored in database 160. In addition, monitoring and feedback platform may generate and store personal baselines for each use. These types of individualized baselines may be useful in generating more accurate evaluations. For example, an individual's baseline oxygen saturation will be different at increasing altitudes or disease states. Change from an individual's baseline is a key clinical variable. As a result, the system provide access to a large data set and provides a consistent, rapid way to incorporate the data into a meaningful value for feedback from families and healthcare providers. Algorithms to incorporate normative standards for reliable sensor data and personal baselines with percent variation from baseline may be implemented to provide rapidly useable data.

The baseline profiles may be related to ranges of awake movement intensity e.g., resting, walking or running. Movement intensity and states are useful in defining health and wellness. For example, movement and exercise have been showed to define pulmonary statues of multiple disease states (Chronic Obstructive Lung Disease (COPD), Interstitial Lung Disease (ILD), asthma, Cystic Fibrosis (CF), and measured through supervised office based testing of 6 minute walk testing (6MVVT) and pulmonary rehabilitation. 6MVVT can correlate with pulmonary function data. For healthy children and those with chronic disease the ability to play, exercise and do physical activities is an essential part of normal childhood. Children that have exercise intolerance are not well and this is frequently an indicator explored in office visits.

Figure 2:
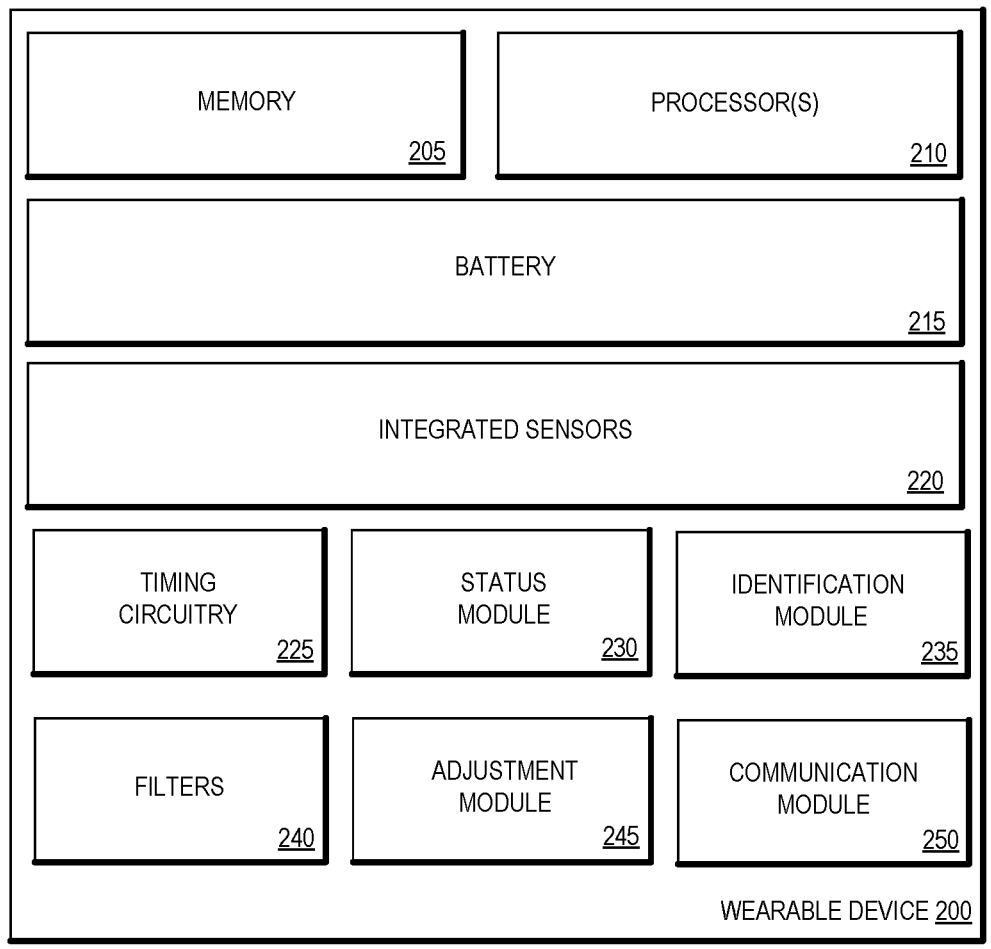
FIG. 2 illustrates a set of components within a wearable monitoring device 200 according to one or more embodiments of the present technology.

FIG. 2 illustrates a set of components within a wearable monitoring device 200 according to one or more embodiments of the present technology. As shown in FIG. 2, wearable monitoring device 200 may include memory 205 (e.g., volatile memory and/or nonvolatile memory), one or more processors 210 for executing processing instructions, battery 215, and integrated sensors 220 for measuring environmental and/or physiological data. Additional components such as timing circuitry 225, status module 230, identification module 235, filters, 240, adjustment module 245, and/or communication module 250.

Processor(s) 210 are the main processors of wearable monitoring device 200 which may include application processors, baseband processors, various coprocessors, and other dedicated processors for operating wearable monitoring device 200. These processors along with the other components may be powered by battery 215. The volatile and nonvolatile memories found in various embodiments may include storage media for storing information such as processor-readable instructions, data structures, program modules, or other data. Some examples of information that may be stored include basic input/output systems (BIOS), operating systems, and applications.

In some embodiments, integrated sensors 220 may be printed, sewed, attached, built or otherwise integrated into the wearable monitoring devices at specific anatomical locations consistent with obtaining the most accurate measurements. For example, in some embodiments, sensors 220 may include optical sensors, gyrometers, GPS, particulate sensors, temperature sensors, microphones, video recorders, heart rate monitors, pulse oximetry sensors, respiration sensor, accelerometers, environmental particulate matter sensors, moisture sensors, and the like. Sensors 220 may be controlled by timing circuitry 225 and configured to gather data (e.g., periodically every 5-10 seconds or at intermittent time intervals).

Status module 230 can monitor the health of the sensor network. For example, the status module can monitor when the sensors associated with the wearable device are malfunctioning or exhibiting anomalous behavior. In some embodiments, the status module 230 can report the health of the sensors associated with the wearable device to the monitoring and feedback platform. The sensors monitored by the status module 230 can monitor physiological data and/or environmental data of an environment in the vicinity of the wearable device 200.

Identification module 235 may be able to provide a unique identifier to external devices and/or securely identify remote devices which wearable device 200 may communicate with. Such an identifier can be based on the MAC address of the device or an IP address associated with the device. In some embodiments, the identification module also performs authentication of the remote devices based on one or more cryptographic algorithms. In some implementations, if the identification module 235 fails to authenticate an external device, then the identification module terminates communications with the external device. In some embodiments, the identification module 235 maintains a white list of allowable external devices and a blacklist of external devices that have failed authentication a certain number of times.

Filters 240 may be software and/or hardware filters which can be used to filter the data. In some cases, the filters being applied to the data may be dynamically adjusted by adjustment module 245. The filters can remove noise or other undesirable artifacts from the captured physiological and/or environmental data.

Communication module 250 can be used to relay the data (e.g., streaming or in batches) to a wireless device or mobile platform for processing. In some embodiments, the data may be stored locally until wearable device 200 is in transmittable range. Communication module 250 may include a network interfaces (e.g., Bluetooth Interface or Network Communication Interface, which enables the wearable device to communicate by transmitting and receiving wireless signals using personal area network or licensed, semi-licensed or unlicensed spectrum over a telecommunications network). Physiological information sensed from a patient is sent to a remote server by either a wearable device or a mobile device worn coupled to a user. In some embodiments, a local hub or a router within wireless range from the user can connect to the remote server and transmit the physiological information. After the physiological information is received by the remote server, this information is stored on the server. In some embodiments, this information is first processed by a pre-processing algorithm to eliminate artifacts in the information. In some embodiments, machine learning algorithms are applied on the pre-processed information. Examples of machine learning algorithms can include, but not limited to, feature extraction, patent recognition, and causality analysis. (See FIG. 13 for an example).

Figure 3:
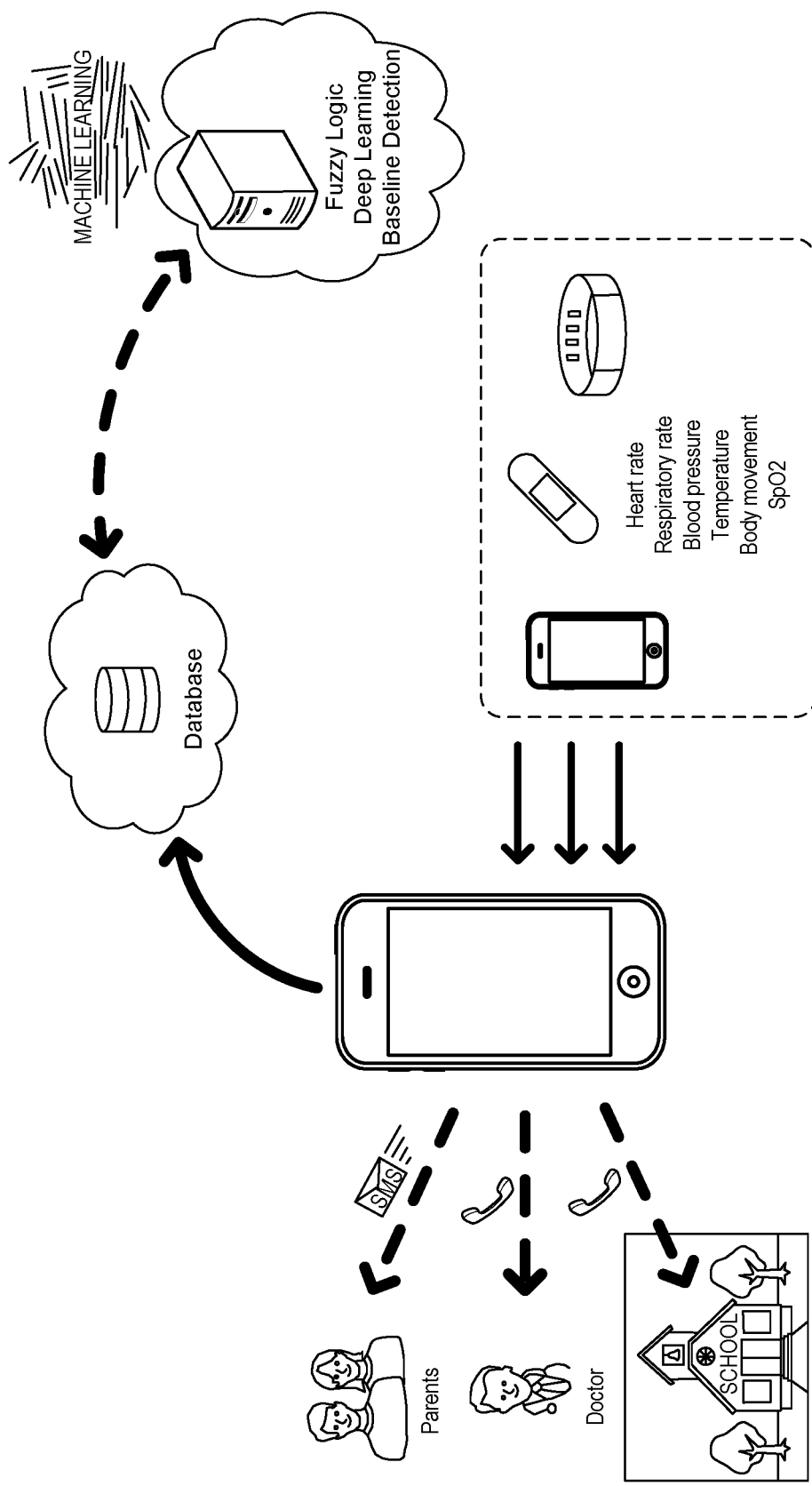
FIG. 3 illustrates a set of components associated with a monitoring and feedback platform according to one or more embodiments of the present technology.

FIG. 3 illustrates a set of components associated with a monitoring and feedback platform according to one or more embodiments of the present technology. For example, FIG. 3 indicates that a wearable device or a mobile device attached to the user monitors physiological data such as a heart rate, a respiratory rate, a blood pressure, a temperature, a body movement, and SpO2 levels to detect the onset of a pulmonary event for the user. Such data is sent to the monitoring and detection platform where the data is analyzed using machine learning methodologies (e.g., fuzzy logic or deep learning) with reference to a baseline health profile of the user). The machine learning methodologies, the baseline health profile, and the outcome of the analysis of the physiological data can be stored in a database. After the analysis is complete, the outcome of the analysis is sent to the parents, the doctor, or a school of the user. Various channels of communication can be used to report the outcome. Examples of such channels include SMS alerts, MMS alerts, automated phone calls, emails, and the like.

Figure 4:
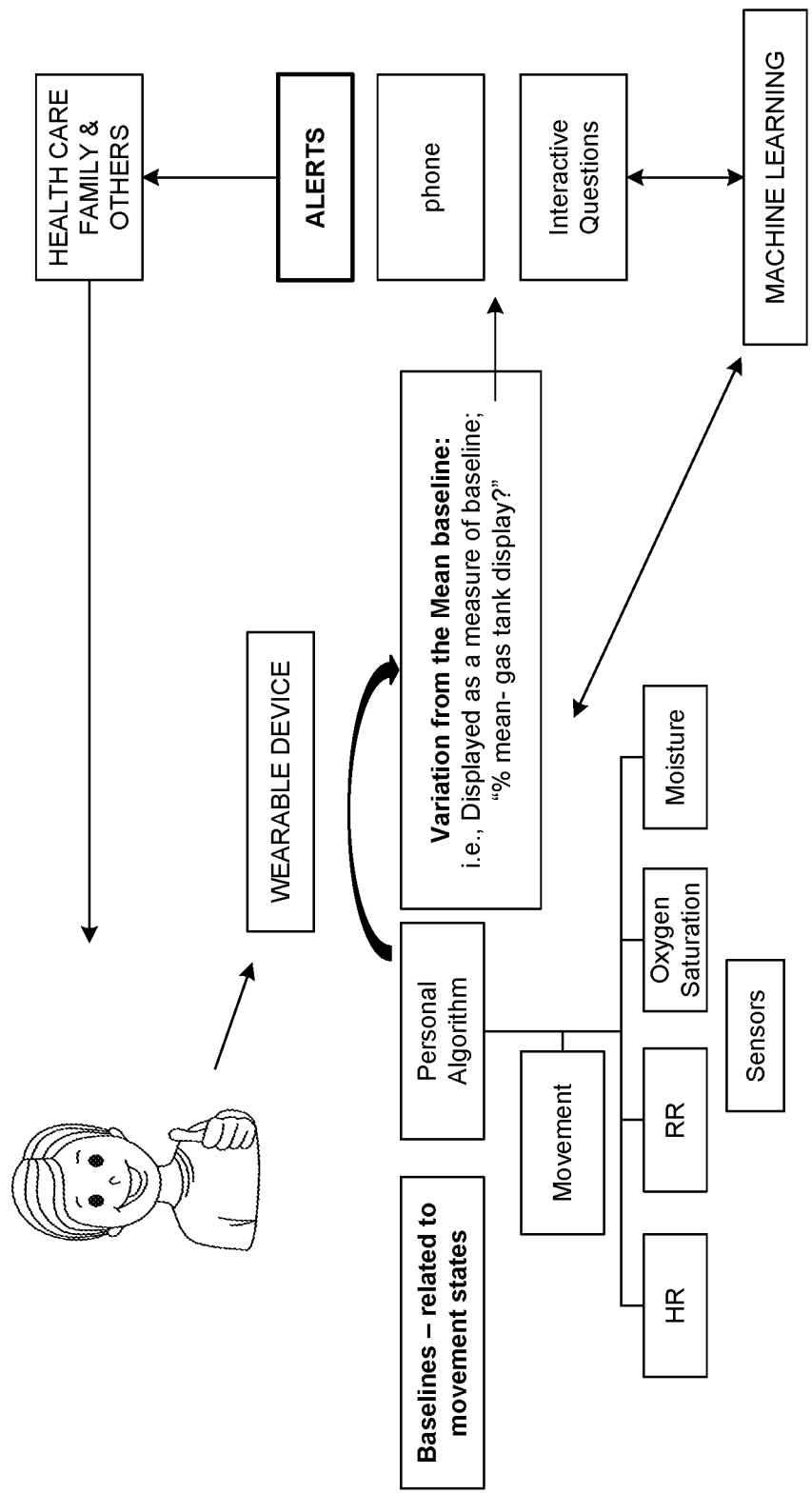
FIG. 4 is a block diagram illustrating various interactions between components of a health monitoring system.

FIG. 4 is a block diagram illustrating various interactions between components of a health monitoring system. As illustrated in FIG. 4, the child wears a reliable sensor that monitors HR, RR, oxygen saturation, movement, temperature/moisture, and the like. In accordance with various embodiments, the system can use software to establish a physiological baseline for a patient by measuring the above parameters during the steady state of the individual. Baseline data is recorded for this individual over a specific period of monitoring time in different states: awake at rest, awake with different intensities of movement (e.g., walking and running), and sleeping.

Once baseline data is recorded, the device can monitor changes from baseline as x % of baseline based upon algorithm development that interprets sensor variables in relationship to movement. In some embodiments, anomaly detection algorithm can be employed to detect when a patient's physiological information indicates an unhealthy condition. Example of such algorithms can include Bayesian network-based approach, multilayered perceptron (artificial neural networks), decision tree, support vector machines algorithm, and online-machine learning algorithms. The period of monitoring time to report X % of baseline can be set to different time frames over a 24 hour period depending upon wellness or disease states. If health status deviates from baseline an alert will be wirelessly transmitted to portable electronic devices of caregivers such as parents and/or medical professionals.

Once alerts are triggered, interactive survey questions may be sent back to the portable device from the caregiver's electronic device. This real time feedback and monitoring with simple measurements is invaluable to families and health care providers to understand changes in disease status. For example, an asthmatic child at rest could have an increase heart noted over baseline and when surveyed from a menu of possible causes the response may be administration of bronchodilators that are known to increase HR, resulting in a physiological method to determine bronchodilator use. With increased use and advanced machine learning the family and health care providers will become more attuned to the meaning of the individual's X % deviations from baseline. Should extremes in signal variables (significant low oxygen levels) or continued deterioration from x % of baseline develop, then families or health care providers can be notified, provided with an intervention, and then the interventions monitored by caregivers to assure a return to baseline.

A wellness scenario could also exist in that a child begins to train for soccer or track. Baseline sensor physiology is measured and over time changes in distance and decreases in HR and RR are noted from baseline to determine improvements in training and health. This could also be used for to track the health of a child with obesity and metabolic syndrome.

As described above, the wearable device may consist of a compression-type arm sleeve, arm cuff, wrist band, shirt, chest patch, eye piece, ear piece, headband, leg band, or the like. Sensors would be printed, sewed, attached, built, or otherwise integrated into the wearable at specific anatomical locations consistent with obtaining the most accurate measurements. The wearable can include optical sensors, gyrometers, GPS, particulate sensors, temperature sensors, memory, software and a battery. The sensors would generate data every 5-10 seconds (or, at intermittent time intervals) and relay it to the wireless device for processing or store it until the wearable is in transmittable range.

Depending on the end user, varying information may be displayed on the electronic device of the caregivers. For the at-home user, a parent would see a dashboard indicating the child's health score (1-100) as a percentage of baseline with a Red/Yellow/Green indicator or a gas tank display of full-to-empty. A physician may see readouts of the physiological parameters in addition to the health score and R/Y/G indicator.

The system may include various algorithms that present data as deviations from baseline state, integrated sensor analysis taking into account interdependency of data, especially movement and interactive survey at the time of the alert to get real time feedback on issues. The interactive survey may change the questions based on a variety of factors such as current vital signs, baseline data, particular sensor readings, and/or other factors. The system can be implemented in a number of ways to include: Use in the home, day care or school setting for parents to monitor children at risk of pulmonary events. The device can monitor a child's physiology and predict likelihood or detect early onset of a pulmonary event. The device could also be used at home or in the clinical setting to identify patients that are experiencing illness, or responding (or not) to therapy. It can be used in discharge planning for monitoring high risk patients. It could be used to track adherence to medications and track outcome measures for clinical studies. It can be used to determine health fitness improvement in elite athletes or those with metabolic syndrome or obesity. It can be used to program ideal safe exercise programs and evaluations (6MWT) in the community.

Respiratory rate measurements from Photoplethysmography (PPG) have been investigated and can be further developed. As machine learning and computing increase more accurate algorithms will be developed. Also the interactive surveys may also have the feature of capturing video of the physiologic disturbance, especially in younger children who cannot respond to survey questions. Ultimately sensors of temperature and moistures will be used to predict stress levels in children for population health and toxic stress. Furthermore with more advance information increased understanding of disease states will occur through access to this real time and detailed physiology in children.

Figure 5:
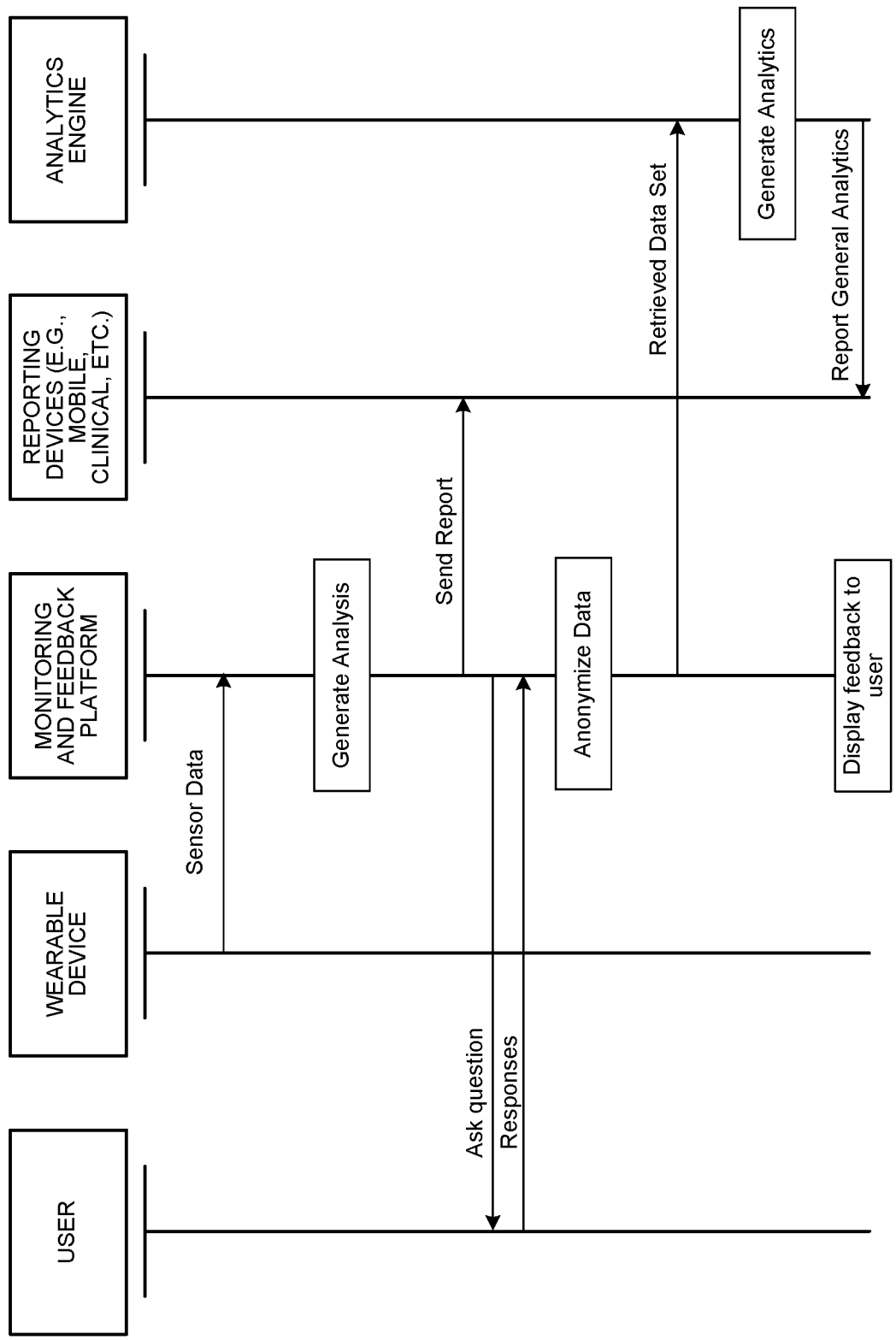
FIG. 5 is a sequence diagram illustrating an example of the data flow between various components of a health monitoring system according to various embodiments of the present technology.

FIG. 5 is a sequence diagram illustrating an example of the data flow between various components of a health monitoring system according to various embodiments of the present technology. As illustrated in FIG. 5, wearable devices collect a variety of data using various sensors. The sensor data (or a filter version) may be transmitted to a monitoring and feedback platform where an analysis is generated. In accordance with some embodiments, the analysis generated by the monitoring and feedback platform may be based on individualized baseline profiles that have been previously generated. These individualized baseline profiles can be compared against the current sensor data and used to generate a health report. Once generated, the monitoring and feedback platform can send the health report to a reporting device (e.g., a mobile phone running an application, a clinical device, etc.) where a caregiver (e.g., parent, medical professional, etc.) can evaluate the data. The health reports may include video of current activity, transmitted using SMS or MMS alerts, and the like. In some embodiments, monitoring and feedback platform may generate an anonymized set of data which can be used by analytics engine to generate various analytics. This can be useful, for example, in determining the effectiveness of different treatments. In some embodiments, a user coupled to the wearable device can ask questions to the monitoring and feedback platform, and receive responses for the questions asked. In some embodiments, the monitoring and feedback platform displays feedback to the user, the feedback including physiological health parameters of the user and the outcome of the analysis of such parameters.

Figure 6:
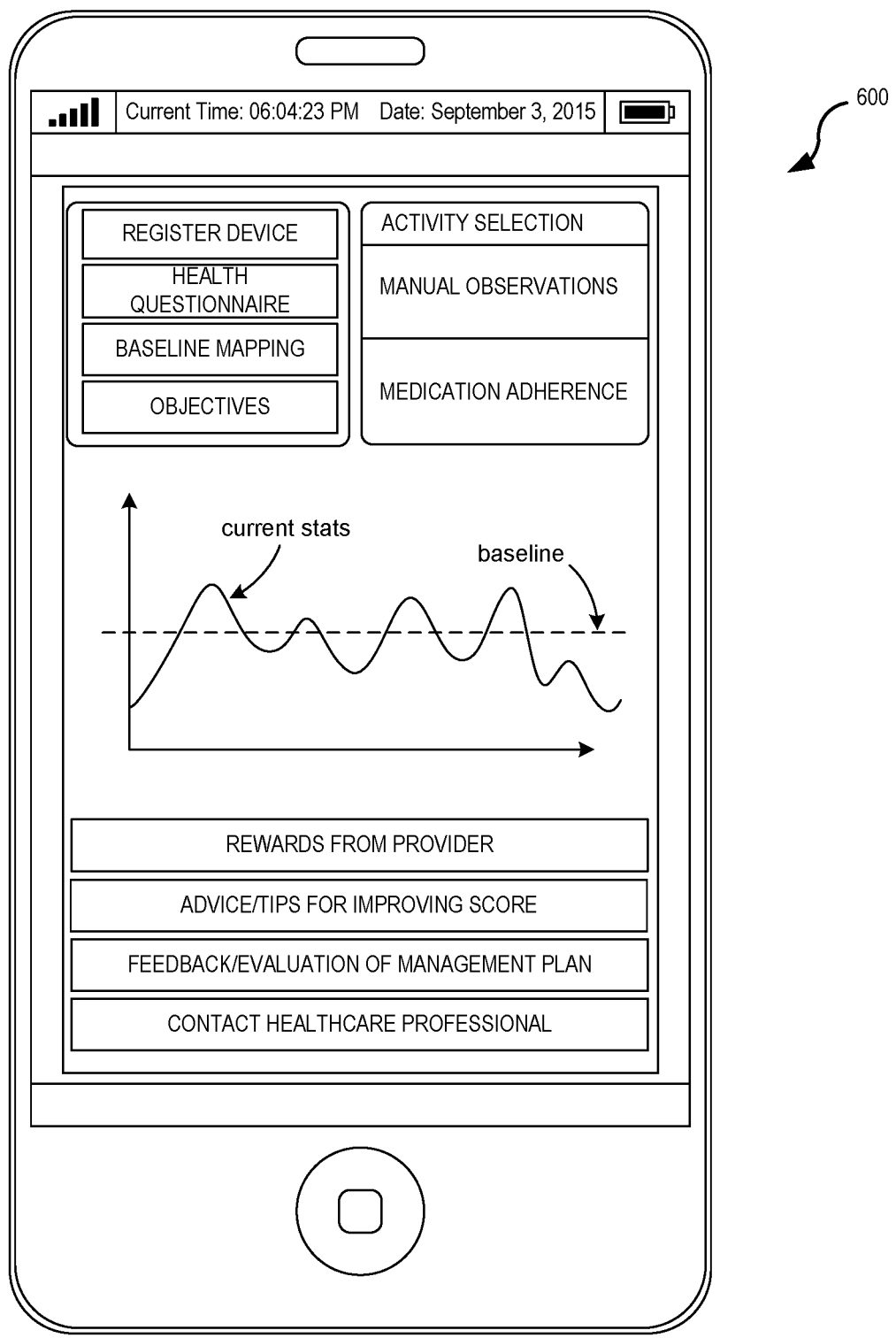
FIG. 6 is an example of a graphical user interface that may be used in accordance with various embodiments of the present technology.

FIG. 6 is an example of a graphical user interface that may be used in accordance with various embodiments of the present technology. The interface displays options for registering a wearable device, a health questionnaire, a baseline mapping profile of the user, and one or more health objectives that the user desires to achieve. In some embodiments, the interface can also display an activity selection option for one or more physical activities in which the user wants to participate, an option for manually entering (e.g., by the user) observations pertaining to the user's health or environment, and an option to enter a degree of medical adherence. The interface also displays a graph showing a graph of the current health stats of the user, e.g., over a certain time period with respect to a baseline health profile of the user. In some embodiments, the disclosed technology can provide rewards to a user (e.g., for medication adherence) from a medical services provider or an insurance provider. The interface can also provide tips/recommendations for improving the overall health score of a user. Further, the interface can provide feedback for a user's health management plan and the ability to contact a healthcare professional.

Figure 7:
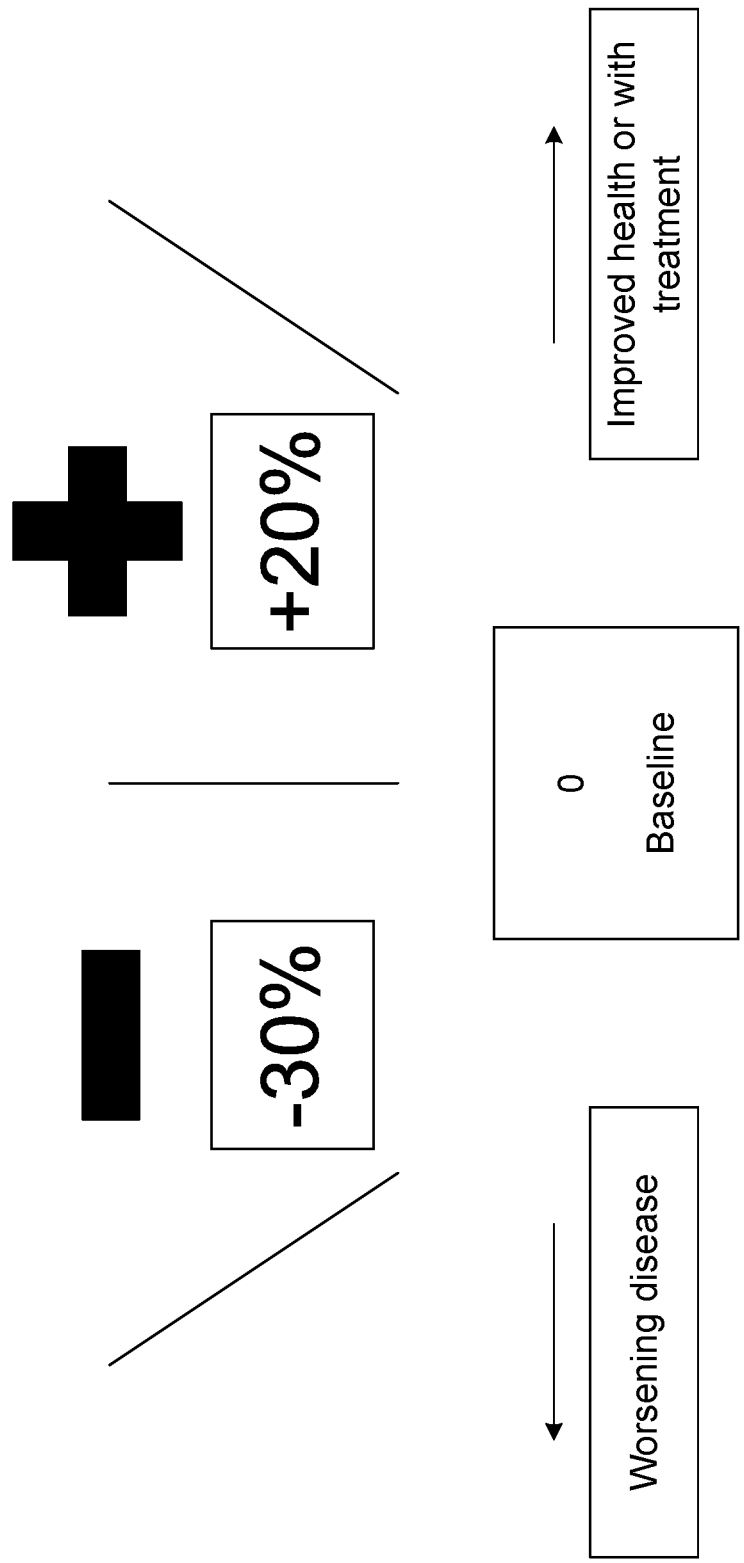
FIG. 7 is an example of a graphical user interface that may be used to provide feedback in accordance with one or more embodiments of the present technology.

FIG. 7 is an example of a graphical user interface that may be used to provide feedback in accordance with one or more embodiments of the present technology. Such a graphical user interface can be implemented at the monitoring and detection platform and/or at an application program running on the wearable/mobile device. The interface displays a percentage improvement of a user's health with respect to a baseline and/or a worsening percentage of the user's health with respect to the baseline.

Figure 8:
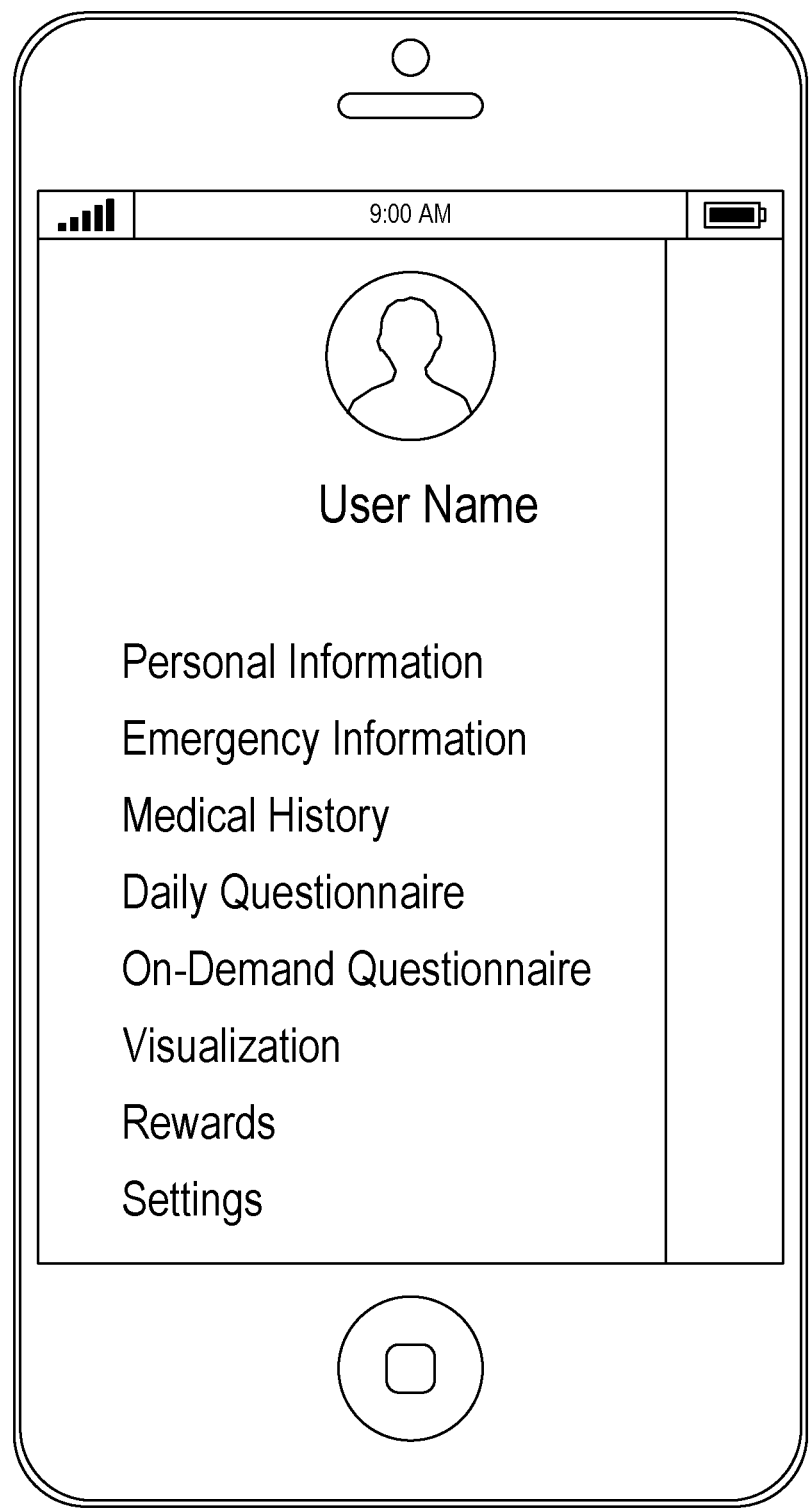
FIG. 8 is an example of a graphical user interface that may be used in accordance with various embodiments of the present technology.

FIG. 8 is an example of a graphical user interface that may be used in accordance with various embodiments of the present technology. The interface displays various menu options such as a user's personal information, emergency information, a user's medical history, a daily questionnaire for the user, an on-demand questionnaire, a visualization of the user's current health status, rewards (or, points) earned by the user, and other configuration settings for the operation of the wearable device or the mobile device. In some examples, the daily questionnaire and the on-demand questionnaire can be directed at the user for the user to complete.

Figure 9:
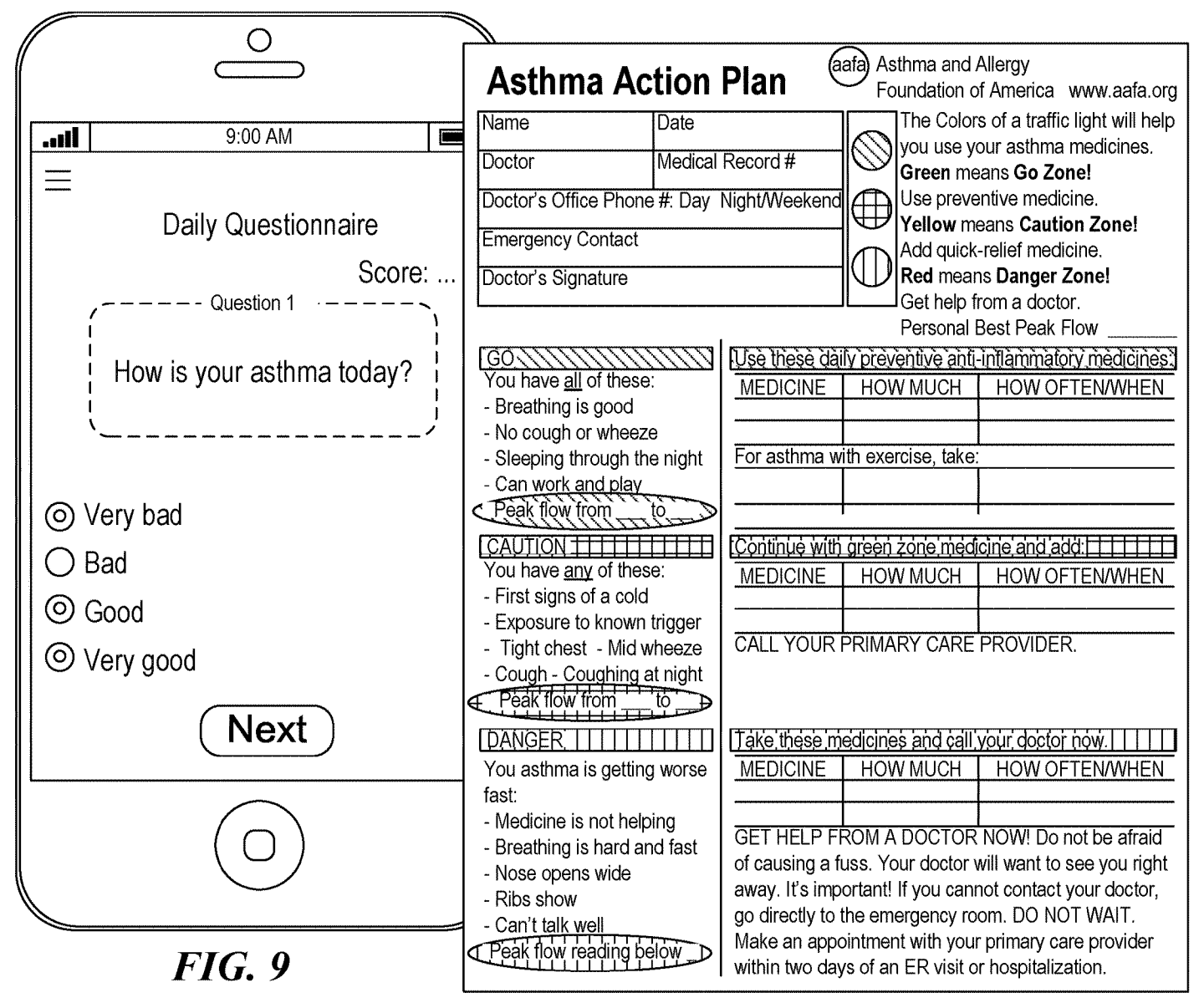

FIG. 9 is an example of a graphical user interface that may be used in accordance with various embodiments of the present technology. The interface displays several questions in connection with a daily questionnaire for the user. In some embodiments, these questions can be predetermined beforehand in time or they can be framed in real time. Depending on the response from the user, the interface can provide feedback regarding the user's health and the medications that the user needs to consume. For example, if the user's response is "Good" or "Very good" to the question "how is your asthma today," then the interface provides an indication of which medicine and how much quantity of the medicine does the user have to consume. In some embodiments, the interface provides color coded (e.g., green, yellow, and red) feedback regarding the user's health and also provides a listing of the symptoms or conditions associated with the user's response. In some embodiments, the interface also informs the user the medications that the user needs to consume based on whether or not the user is involved in a physical activity. The interface in FIG. 9 also displays feedback to the user if the user's response is "Very bad" or "Bad." In some embodiments, the interface can provide an indication of next steps to a user, e.g., call a doctor. In some embodiments, after receiving a user's response to the questionnaire, feedback provided to a user is based on real time analysis of a user's health, wherein such analysis is performed by the monitoring and feedback platform. In some embodiments, a wearable device or a mobile device analyzes the user's response to the questionnaire to generate the feedback.

Figure 10:
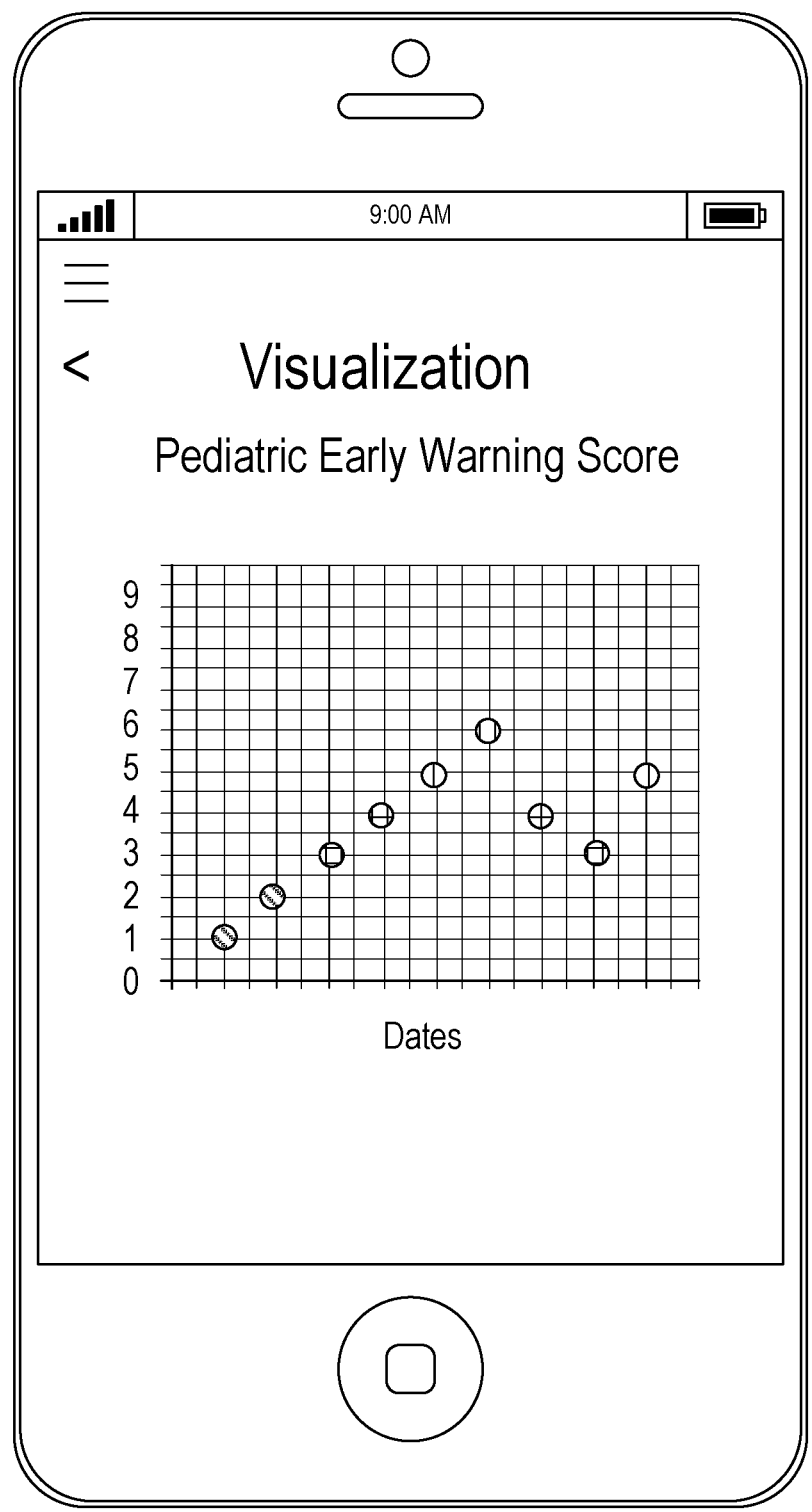
FIG. 10 is an example of a graphical user interface that may be used in accordance with various embodiments of the present technology.

FIG. 10 is an example of a graphical user interface that may be used in accordance with various embodiments of the present technology. The interface includes a graphical visualization of pediatric early warning scores (e.g., representative of a pulmonary event for the user) on a timeline. In some embodiments, a pediatric early warning score can include an aggregate analysis of a user's physiological data and/or environmental data.

Figure 11:
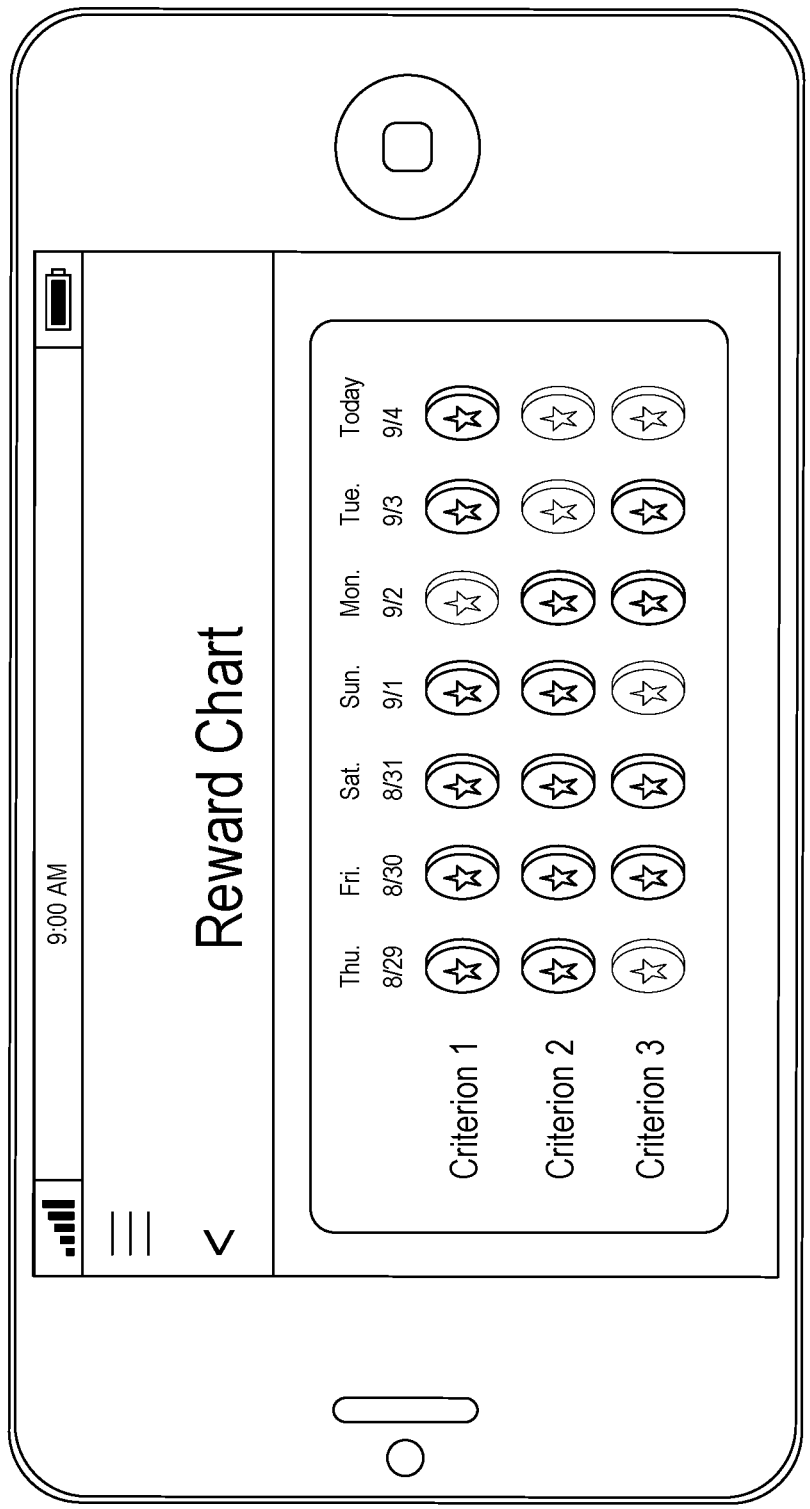
FIG. 11 is an example of a graphical user interface that may be used in accordance with various embodiments of the present technology.

FIG. 11 is an example of a graphical user interface that may be used in accordance with various embodiments of the present technology. The interface displays rewards (or, points) earned by the user as a result of one or more criteria in connection with medication adherence. In some embodiments, the rewards can be displayed as stars or points on the interface.

Figure 12:
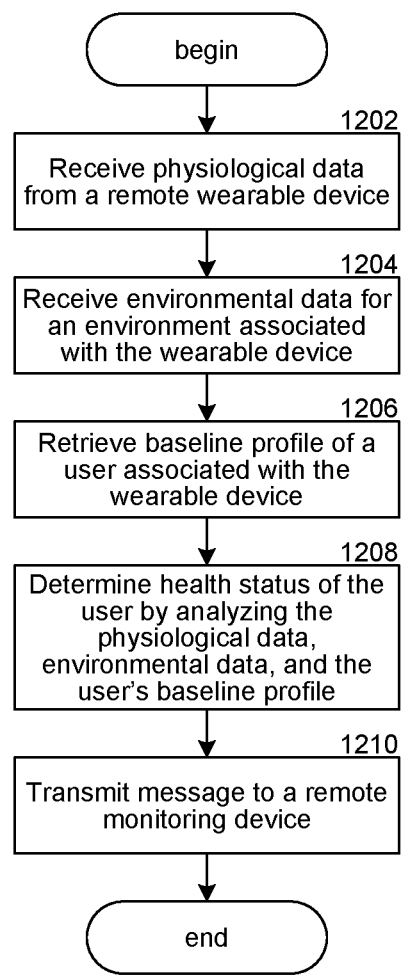
FIG. 12 is a flow chart illustrating steps associated with a monitoring and feedback platform according to one or more embodiments of the present technology.

FIG. 12 is a flow chart illustrating steps associated with a monitoring and feedback platform according to one or more embodiments of the present technology. At step 1202, the monitoring and feedback platform receives physiological data from a (remote) wearable device attached to or carried by a patient/user. At step 1204, the monitoring and feedback platform receives environmental data from an environment surrounding the wearable device. Examples of such data can be amount of pollen in the air, amount of pollutants or gases in the air, amount of oxygen or carbon dioxide in the air, and other environmental data. At step 1206, the monitoring and feedback platform retrieves a baseline profile of the health of the patient. Based on applying one or more adaptive learning algorithms from machine learning methodologies, the monitoring and feedback platform determines (at step 1208) a health status of the patient by analyzing the patient's physiological data, the environmental data, and the patient's baseline health profile. At step 1210, the monitoring and feedback platform transmits a message including a report to the patient, a medical practitioner, or the patient's family. In some embodiments, the message can be received at the patient's wearable device and/or a mobile device.

Figure 13:
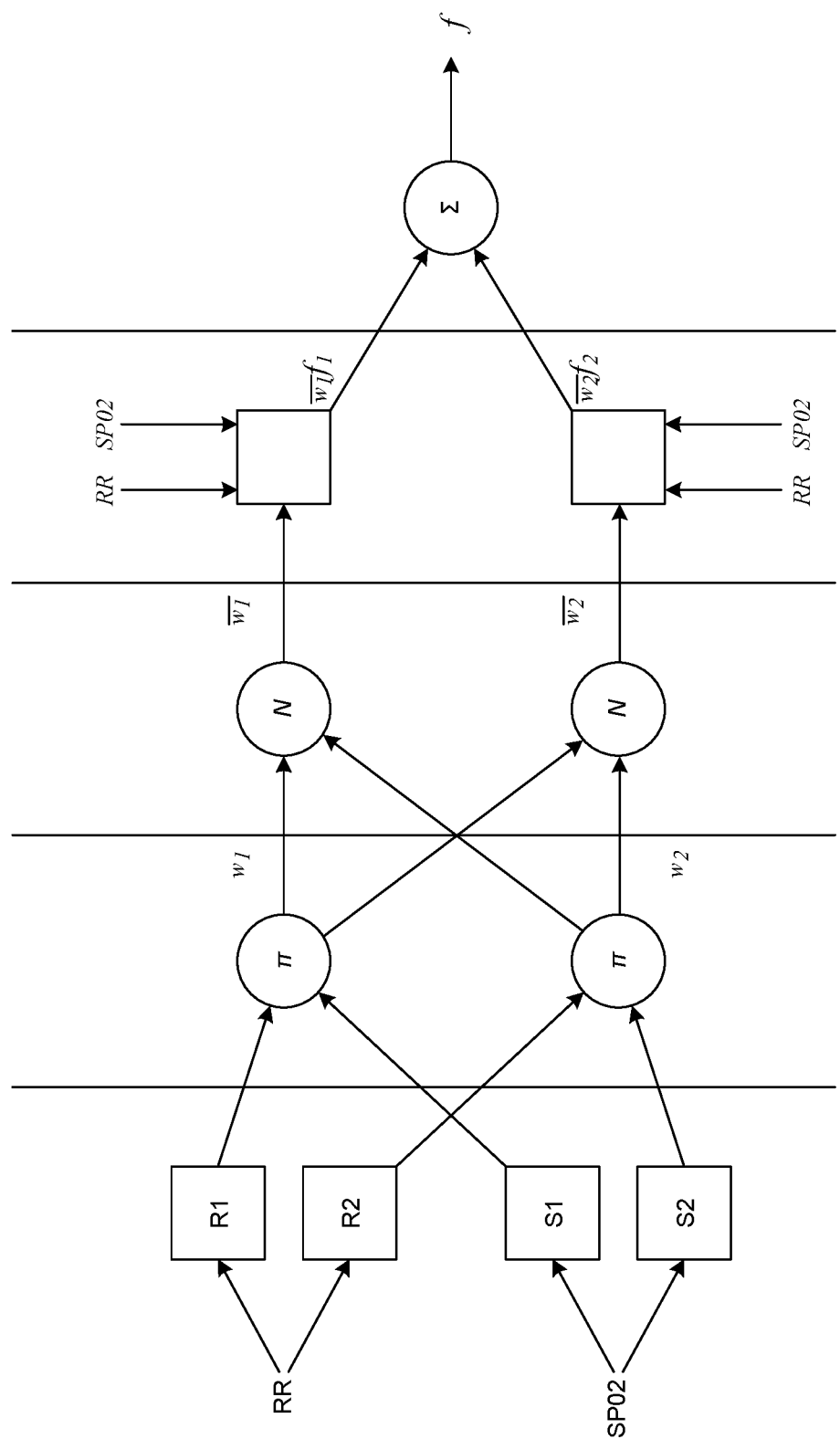
FIG. 13 is a block diagram of a machine learning algorithm based on an adaptive neuro-fuzzy inference system associated with a monitoring and feedback platform according to one or more embodiments of the present technology.

FIG. 13 is a block diagram of a machine learning algorithm based on an adaptive neuro-fuzzy inference system associated with a monitoring and feedback platform according to one or more embodiments of the present technology. FIG. 13 illustrates an example in which a 3 layer neural network is constructed to calculate the importance of each physiological information on patient's health condition. Such a neuro-fuzzy inference system can be integrated into the machine learning algorithms to analyze a patient's physiological data and/or the environmental data for an environment surrounding the patient.

FIG. 14 is an example evaluation of vital data regression model according to one or more embodiments of the present technology. For example, such evaluation is based on a revised Seguno Fuzzy model. Assuming that the model has six (6) rules and five (5) inputs denoted in1, in2, in3, in4, and in5, a test data can first provide six (6) corresponding output according to the following six (6) rules:

If (in1 is in1cluster1) and (in2 is in2cluster1) and (in3 is in3cluster1) and (in4 is in4cluster1) and (in5 is in5cluster1) then (out1 is out1cluster1)

$$f''=2.294p''-0.1055p-+0.899p0-0.12933p2-2.3706p5$$

If (in1 is in1cluster2) and (in2 is in2cluster2) and (in3 is in3cluster2) and (in4 is in4cluster2) and (in5 is in5cluster2) then (out1 is out1cluster2)

$$f-=-1.2655p''+0.7180p-+0.3677p0+0.2704p2+0.5372p5$$

If (in1 is in1cluster3) and (in2 is in2cluster3) and (in3 is in3cluster3) and (in4 is in4cluster3) and (in5 is in5cluster3) then (out1 is out1cluster3)

$$f0=-1.2255p''+59.2561p--0.0084p0+0.0278p2-22.1520p5$$

The next two rules can be similarly set up. Accordingly, the final output is:

$$f = \frac{\sum_{i=1}^{6} w_i f_i}{\sum_{i=1}^{6} w_i}$$

where $w_i$ is the weight of each rule and $f_i$ is its corresponding output. In some embodiments, the weight $w_i$ is based on its membership function of each input. That is, $$w_i = \prod_{j=1}^{5} \mu(Pj)$$

In some embodiments, more than one membership function (e.g., in this case 6 membership functions) for one input variable can exist. To estimate the membership function $\mu(Pj)$ the following rule can be utilized. For example, if the first rule states: "If (in1 is in1cluster1)", then the first membership function in the first input can be utilized to obtain its membership value. In another example if the second rule states: "If (in1 is in1cluster2)", then the second membership function in the first input can be utilized to obtain its membership value. If the number of clusters is increased to 100 or 200, the procedure is similar.

In some embodiments, the data is split after their time measurement. Specifically, the data points are grouped for a specific amount of time. For the gap with 10 minutes, due to the lacking number of data points, we have 33 samples for testing (approximately 500 samples in 10 minutes). Therefore, the 30 seconds period is used as the window-based time stamp. The training data can be unaltered whereas in the testing data, all the samples are averaged. Instead of using 70% training, we can 50% training so that there is data for test case. The number of clusters is 100 and 100 epoch for iterations. Accordingly, 24,945 testing data points and 823 testing data points are used.

Figure 15:
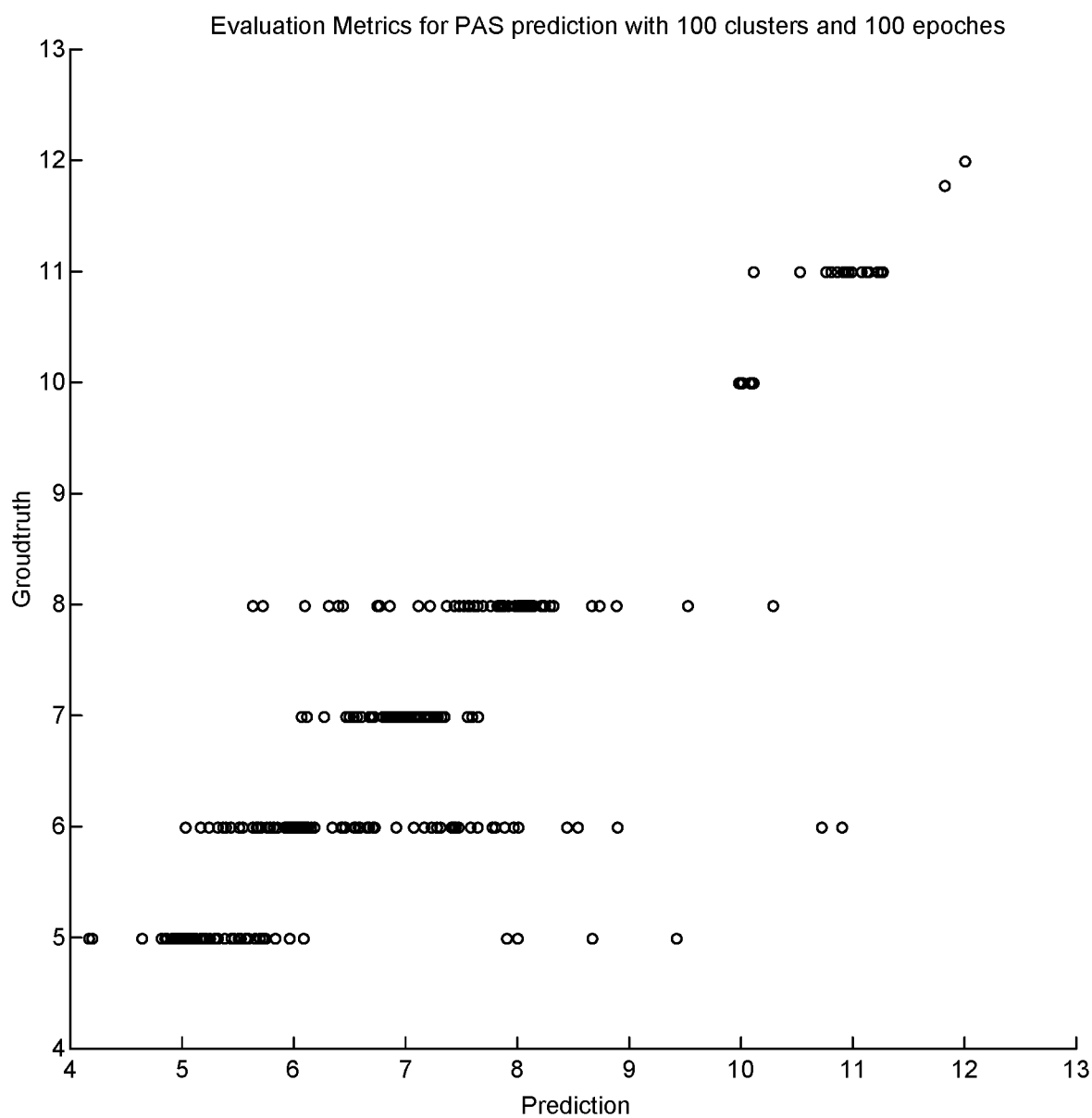
FIG. 15 is an example graph showing evaluation metrics associated with pediatric asthma score (PAS) according to one or more embodiments of the present technology.

FIG. 15 is an example graph showing evaluation metrics associated with pulmonary arterial stiffness (PAS) according to one or more embodiments of the present technology. FIG. 15 indicates that most of the PAS scores lie in the range from [5,8]. Also, the range number 6 has the largest variation. That could be possible because 6 is the borderline between normal and critical condition. However, there are some outliers (e.g., shown in FIG. 13) that are off bounds.

Figure 16:
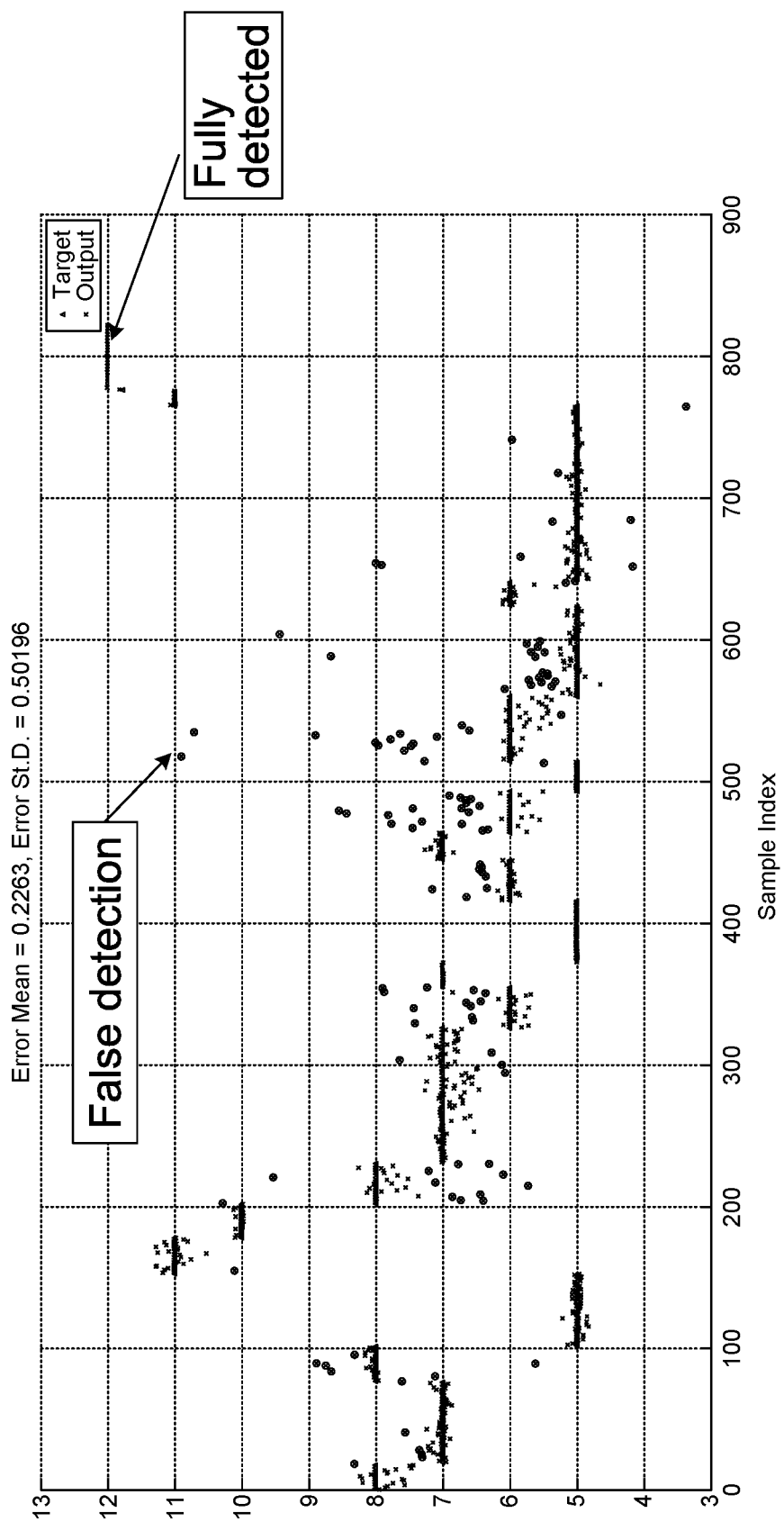
FIG. 16 is an example graph showing outliers in predictions associated with pediatric asthma score (PAS) according to one or more embodiments of the present technology.

FIG. 16 is an example graph showing outliers in predictions associated with pulmonary arterial stiffness (PAS) according to one or more embodiments of the present technology. In FIG. 16, the worst prediction point with its corrected surrounding neighbors for is selected for evaluation.

Figure 17:
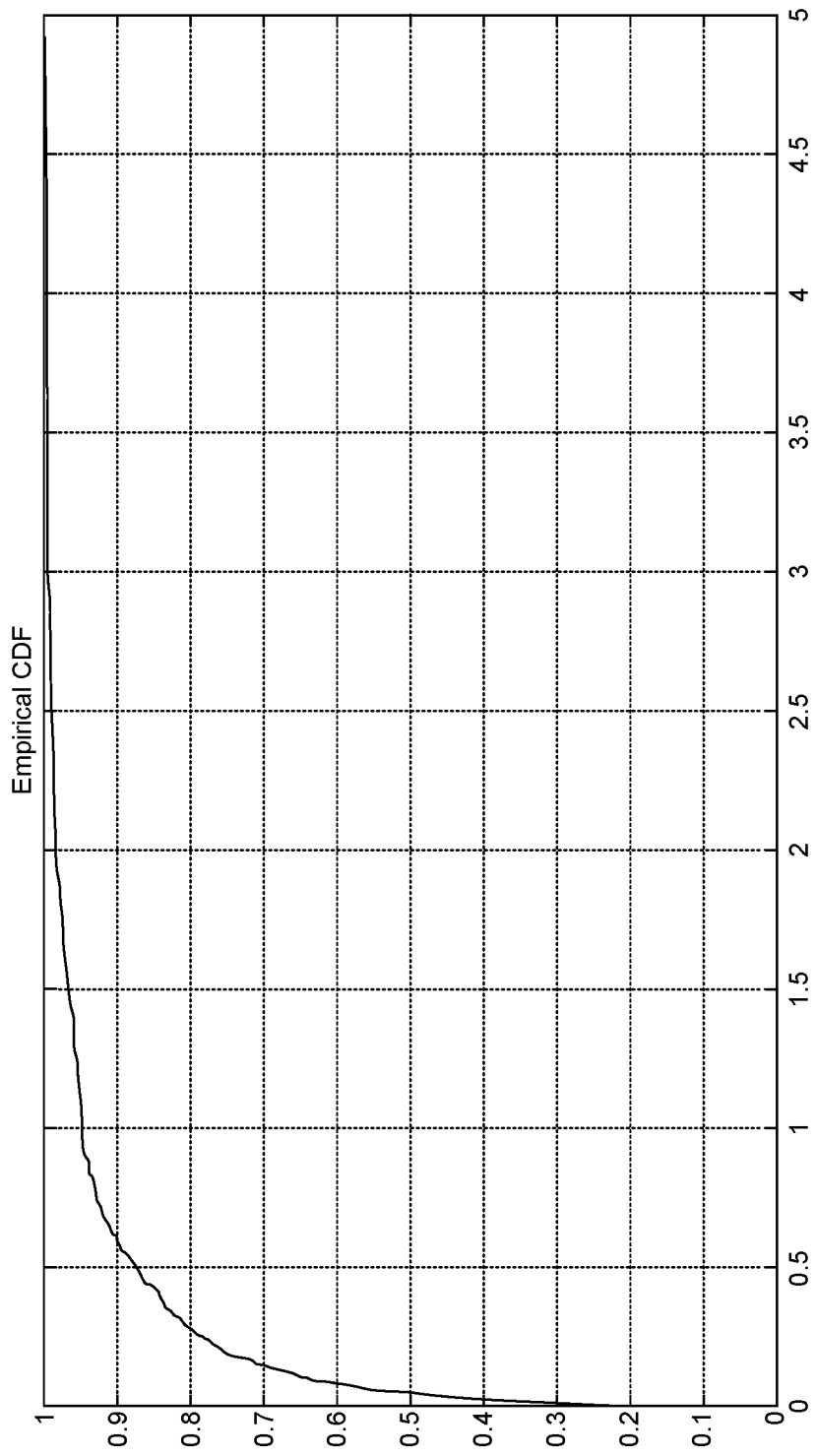
FIG. 17 is an example graph showing a cumulative distribution function (CDF) showing errors in predictions associated with pediatric asthma score (PAS) according to one or more embodiments of the present technology.

FIG. 17 is an example graph showing a cumulative distribution function (CDF) showing errors in predictions associated with pulmonary arterial stiffness (PAS) according to one or more embodiments of the present technology. FIG. 17 indicates there is more than 90% probability that the error will be smaller than 1.0.

FIG. 18 is an example table showing outliers of a Fuzzy model-based time stamp window in predictions associated with pulmonary arterial stiffness (PAS) according to one or more embodiments of the present technology. For purposes of FIG. 18, the worst prediction point with its corrected surrounding neighbors that are good prediction points are selected for evaluation. FIG. 18 demonstrates that RESP has a significant effect in PAS prediction.

Figure 19A:
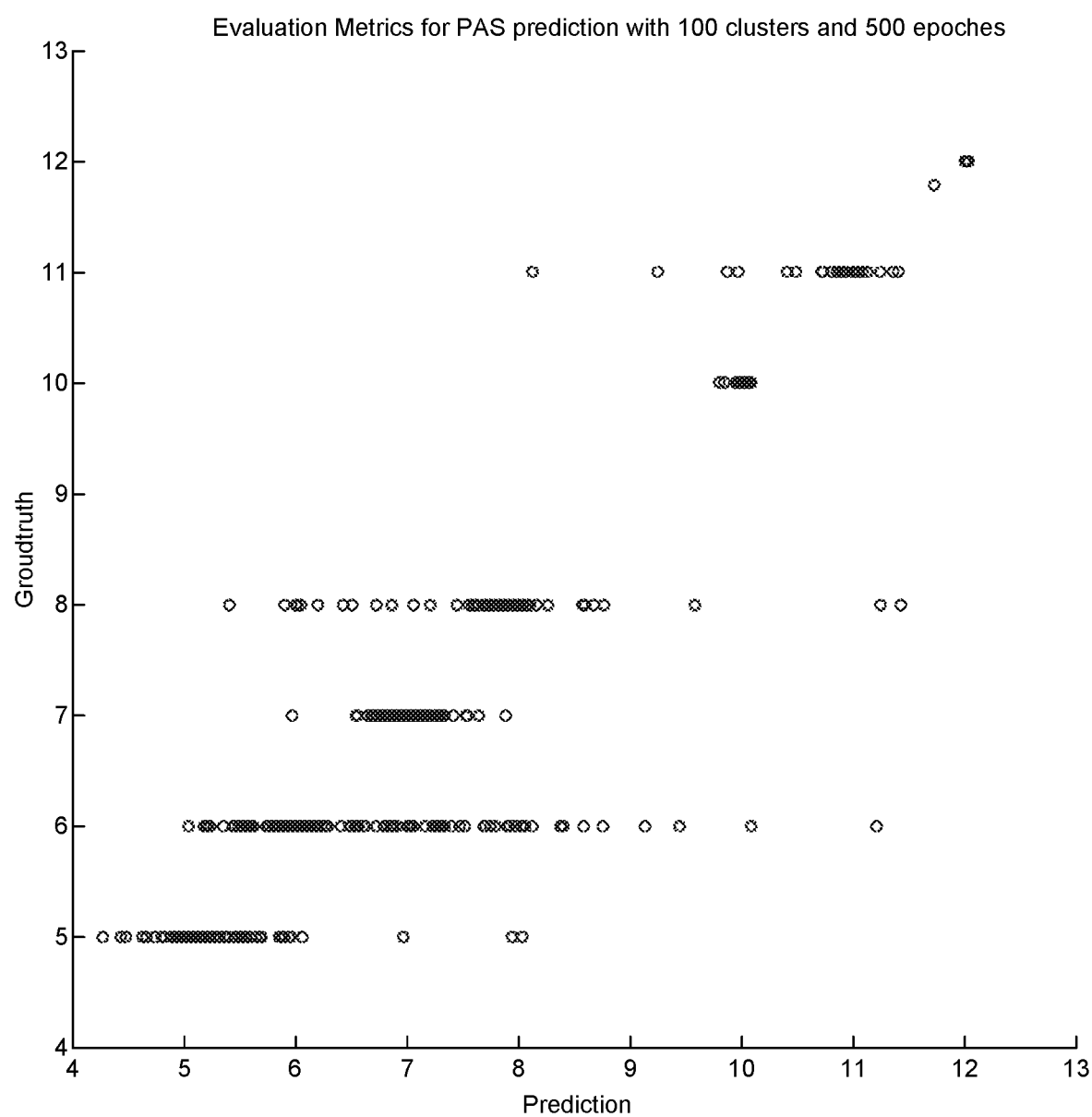
FIG. 19A is an example graph showing evaluation metrics associated with pediatric asthma score (PAS) according to one or more embodiments of the present technology.

FIG. 19A is an example graph showing evaluation metrics associated with pulmonary arterial stiffness (PAS) according to one or more embodiments of the present technology. Specifically, FIG. 19A demonstrates evaluation metrics for PAS prediction with 100 clusters and 500 epochs.

Figure 19B:
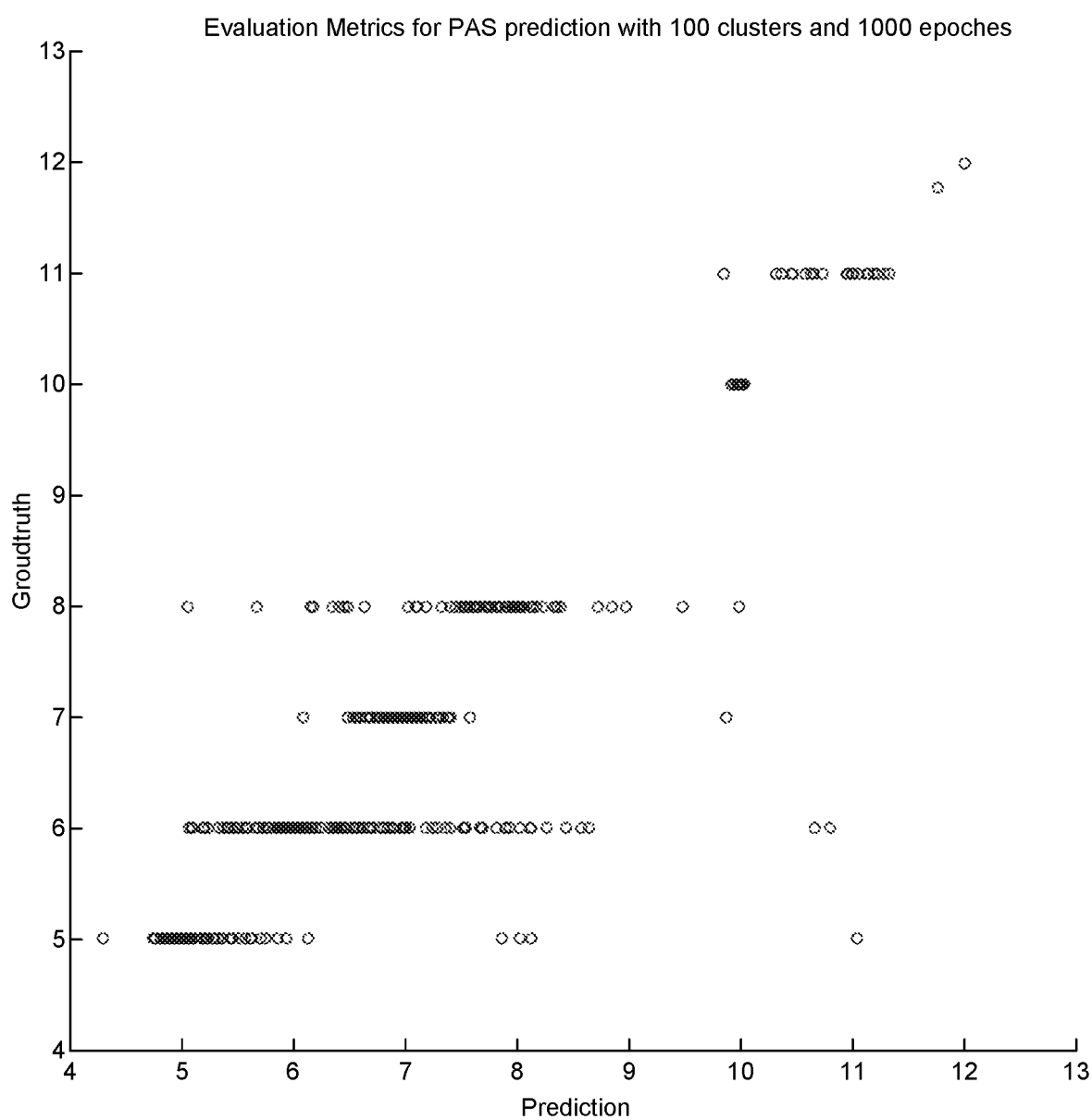
FIG. 19B is an example graph showing evaluation metrics associated with pediatric asthma score (PAS) according to one or more embodiments of the present technology.

FIG. 19B is an example graph showing evaluation metrics associated with pulmonary arterial stiffness (PAS) according to one or more embodiments of the present technology. Specifically, FIG. 19B demonstrates evaluation metrics for PAS prediction with 100 clusters and 1000 epochs.

Figure 20A:
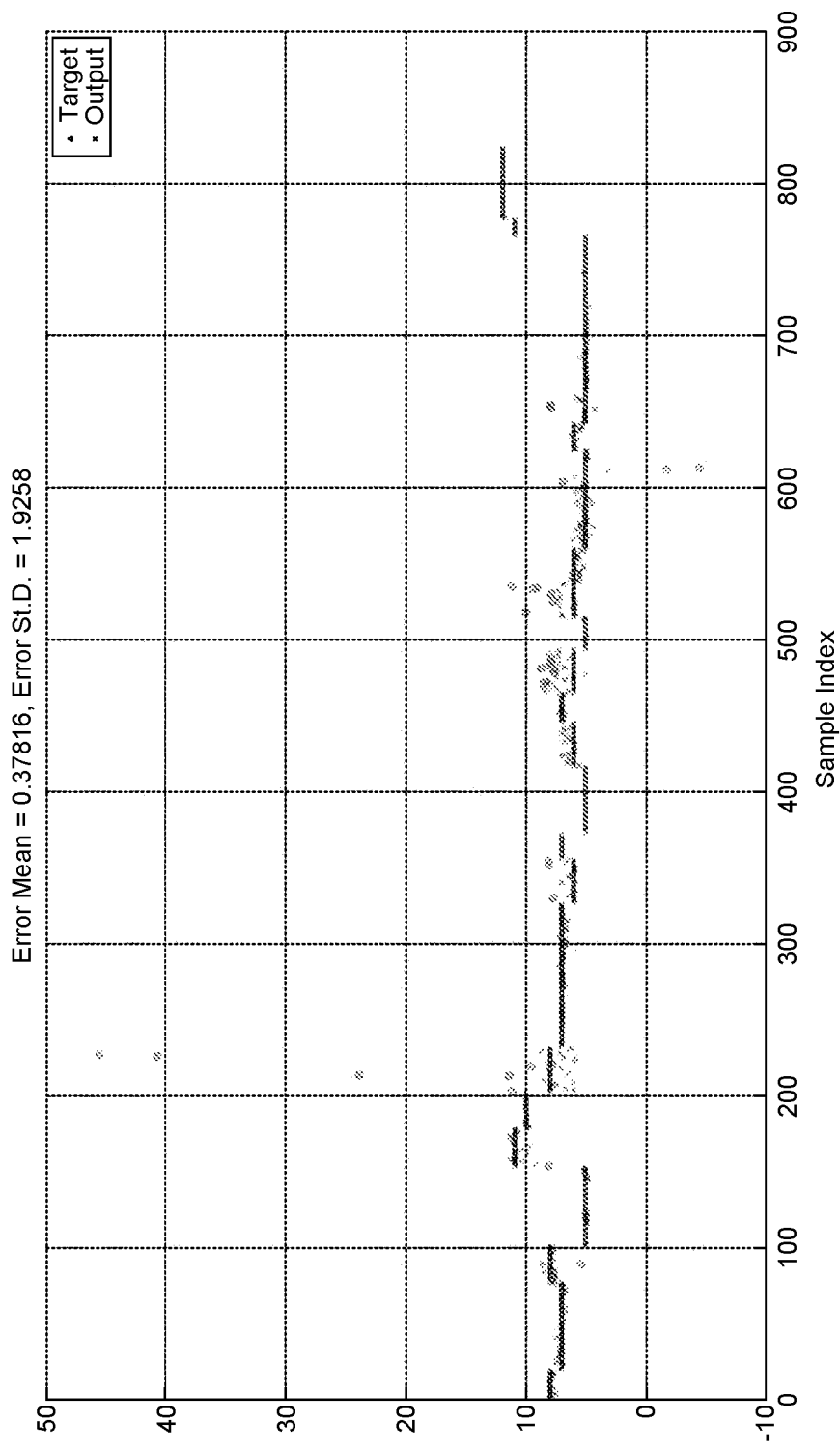
FIG. 20A is an example graph showing results of an experiment with 500 epochs in connection with evaluations associated with pediatric asthma score (PAS) according to one or more embodiments of the present technology.

FIG. 20A is an example graph showing results of an experiment with 500 epochs in connection with evaluations associated with pulmonary arterial stiffness (PAS) according to one or more embodiments of the present technology.

Figure 20B:
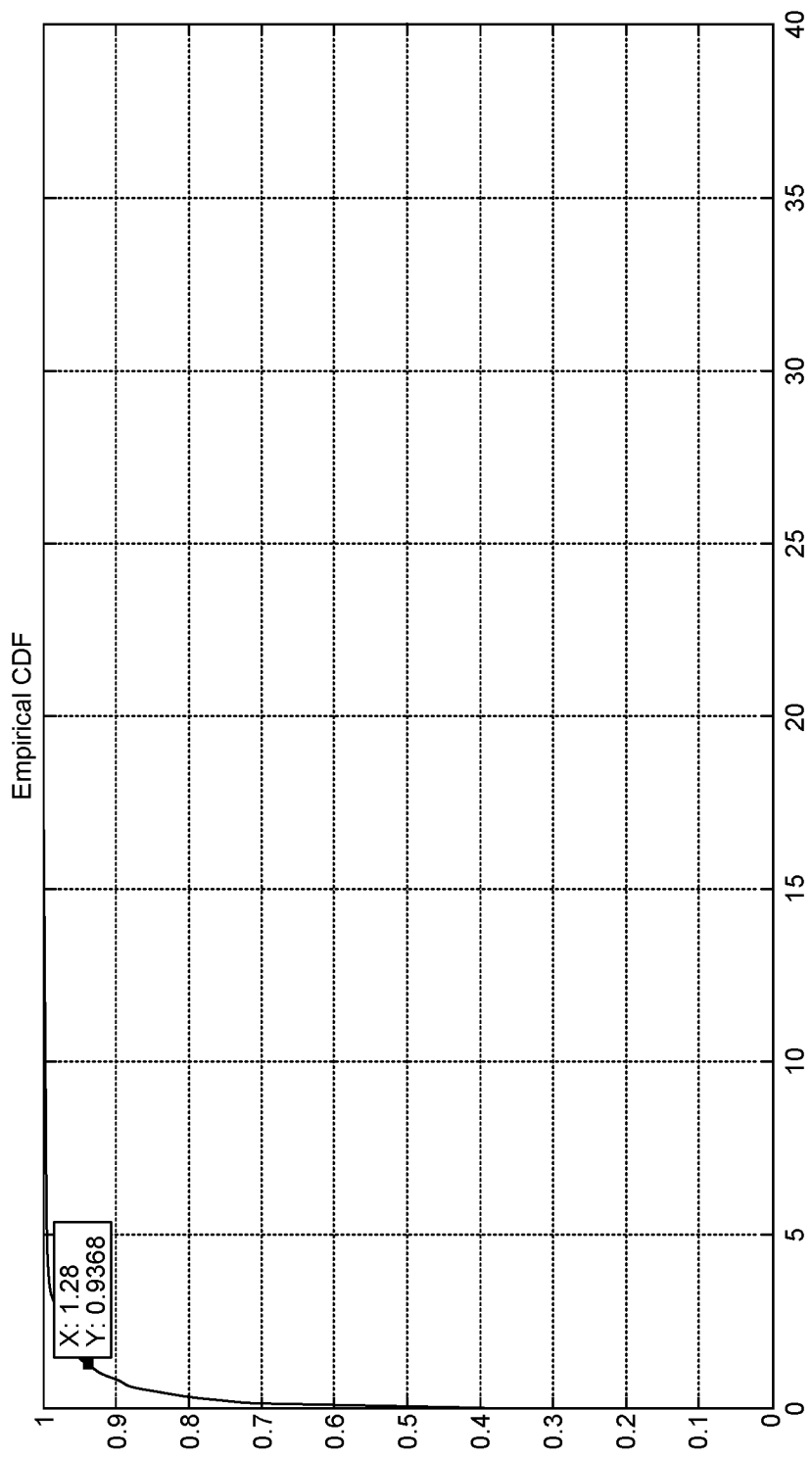
FIG. 20B is an example graph showing a cumulative distribution function (CDF) for an experiment with 500 epochs and showing errors in predictions associated with pediatric asthma score (PAS) according to one or more embodiments of the present technology.

FIG. 20B is an example graph showing a cumulative distribution function (CDF) for an experiment with 500 epochs and showing errors in predictions associated with pulmonary arterial stiffness (PAS) according to one or more embodiments of the present technology.

Figure 21A:
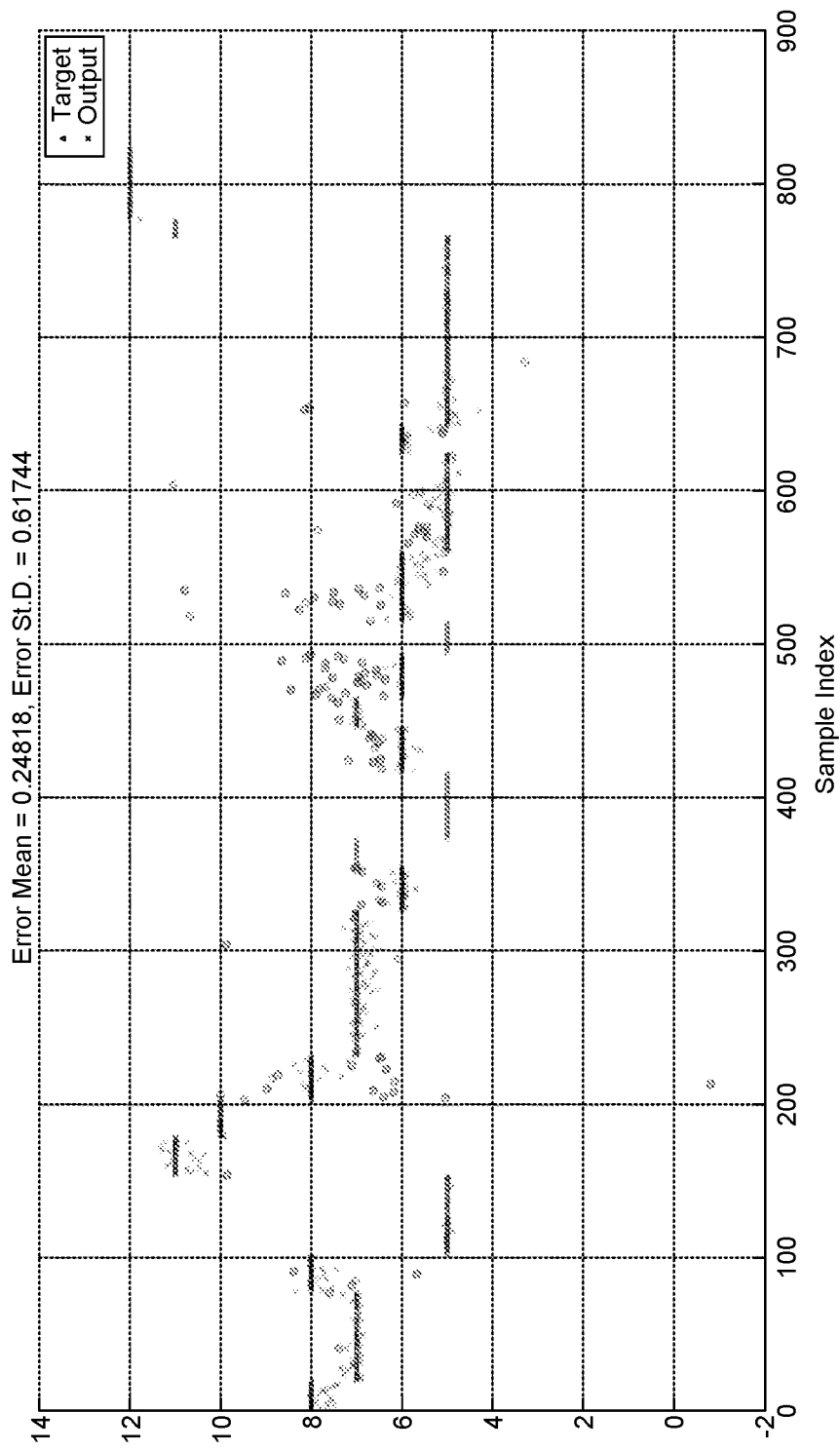
FIG. 21A is an example graph showing results of an experiment with 1000 epochs in connection with evaluations associated with pediatric asthma score (PAS) according to one or more embodiments of the present technology.

FIG. 21A is an example graph showing results of an experiment with 1000 epochs in connection with evaluations associated with pulmonary arterial stiffness (PAS) according to one or more embodiments of the present technology.

Figure 21B:
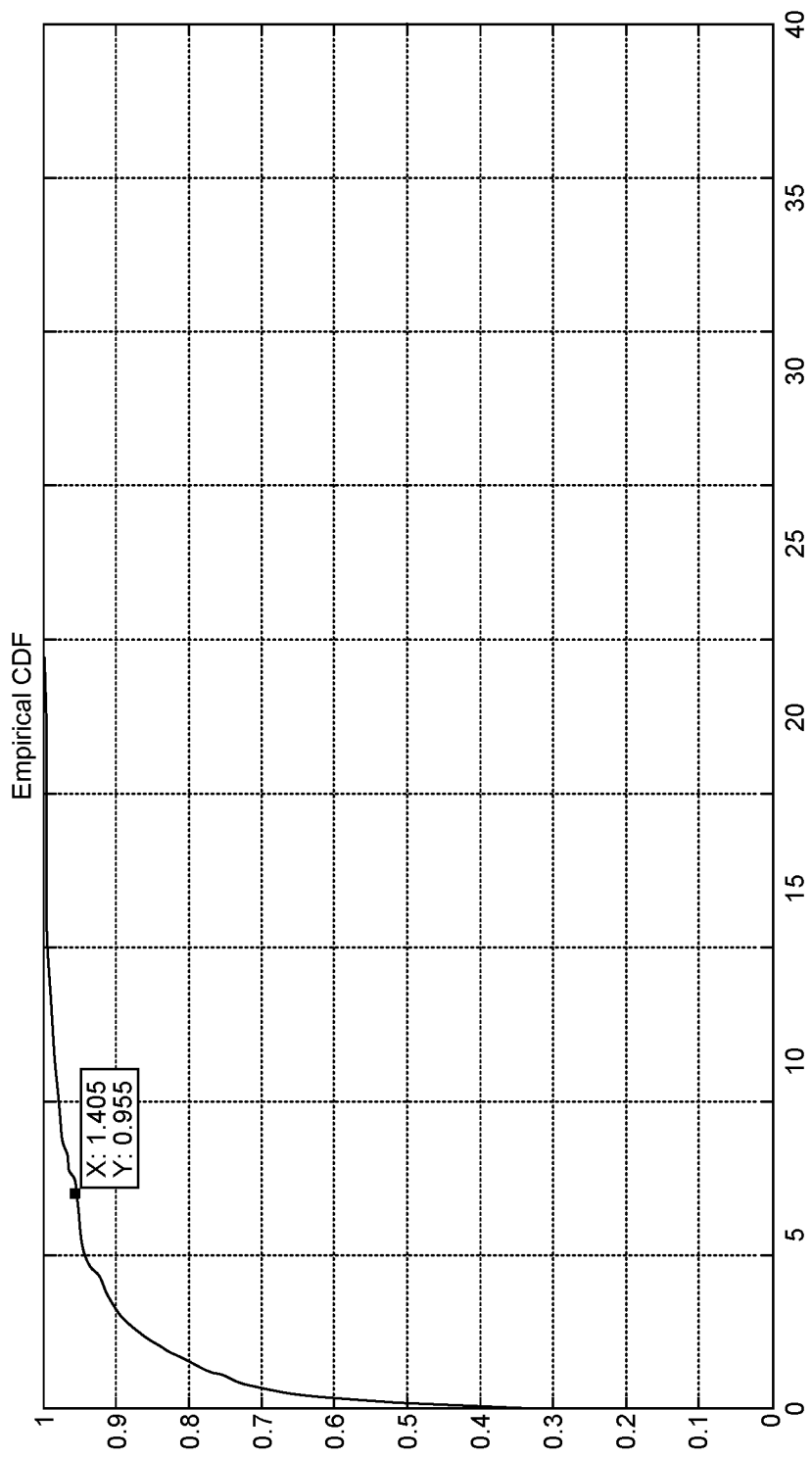
FIG. 21B is an example graph showing a cumulative distribution function (CDF) for an experiment with 1000 epochs and showing errors in predictions associated with pediatric asthma score (PAS) according to one or more embodiments of the present technology.

FIG. 21B is an example graph showing a cumulative distribution function (CDF) for an experiment with 1000 epochs and showing errors in predictions associated with pulmonary arterial stiffness (PAS) according to one or more embodiments of the present technology.

FIG. 22 is an example table showing comparisons of experiments with 100 epochs, 500 epochs, and 1000 epochs in connection with evaluations associated with pulmonary arterial stiffness (PAS) according to one or more embodiments of the present technology. The table demonstrates that increasing the number of epochs can affect to the results of the prediction. Further, in three cases, the number of epochs between 100 and 1000 seems to be similar and better than the 500 cases.

The following six scenarios illustrate examples of the types of situations where the present technology may be utilized, information that can be collected and analysis that can be performed by various embodiments of the present technology.

Scenario #1

With current technology, mild training improvement is not appreciated to further motivate an athlete; subtle or even more significant cardiopulmonary changes may not be perceived by a child or adult to explain poor performance. The following table illustrates an analysis of a 14 year old athlete with asthma using various embodiments of the present technology.

Example - Consumer Market: 14 year old athlete with asthma (Denver 1600 meters) with wearable device

| Activity level* | Rest/ pre-training well baseline | Brisk walk/ pre-training well baseline | max distance or top energy expenditure/ well pre-training baseline | Rest/ well post-training | Brisk walk/ well post-training | max distance or energy expenditure pre training/ well post-training | Rest/ missing asthma meds post-training/ post training | Brisk walk/ missing asthma meds post-training | max distance or energy expenditure missing asthma meds/ post-training |
|---|---|---|---|---|---|---|---|---|---|
| Distance/expenditure | | | 400 yards | | | 600 yard | | | 300 yards |
| HR mean | 80 | 95 | 190 | 75 | 90 | 175 | 90 | 110 | 190 |
| RR mean | 16 | 20 | 35 | 16 | 18 | 30 | 18 | 22 | 40 |

-continued

| Example - Consumer Market: 14 year old athlete with asthma (Denver 1600 meters) with wearable device | | | | | | | | | |
|---|---|---|---|---|---|---|---|---|---|
| Activity level* | Rest/ pre-training well baseline | Brisk walk/ pre-training well baseline | max distance or top energy expenditure/ well pre-training baseline | Rest/ well post-training | Brisk walk/ well post-training | max distance or energy expenditure pre training/ well post-training | Rest/ missing asthma meds post-training/ post training | Brisk walk/ missing asthma meds post-training | max distance or energy expenditure missing asthma meds/ post-training |
| OX Sat mean | 96% | 96% | 98% | 96% | 96% | 97% | 96% | 96% | 95% |
| Temperature mean | 96.8 F. | 97 F. | 99 F. | 96.8 | 97 F. | 98 F. | 96.8 | 97 F. | 99 F. |
| Moisture mean | 0 | +2 | +5 | 0 | +1 | +4 | 0 | +2 | +6 |
| Notification | Baseline data calculated | | | Training impact - aggregate algorithm generated with all the data into % improvement (distance and physiologic) + 5%? Parent or coach notification | | | Training impact lost and worse from baseline - aggregate algorithm generated % off baseline (less distance and worse physiologic) - 10%? Interactive diary - query what's different? Meds or sick? Parent or coach notification to investigate | | |
| Award/ Feedback | | | | Celebration of training improvement Points on a game? Or some graphic reward** | | | Medication restarted*** | | |

*Steps/distance and or calculation of energy output
**The commercial fitness markets whether for elite child or adult athletes or an individual with a poor fitness deconditioned state (obesity) could use the device in this way. There would be many ways to program the devise to look at training effect.
***Asthma changes, even significant ones, may not be felt by children or be subtle but do impact performance and lower thresholds for viral insults and exacerbations; exercise induced asthma is very common in athletes; lower oxygen saturations with exercise off baseline is never normal and an indicator of early disease. The last example in blue could be any child or adult with any cardiopulmonary problem or anyone that could be impacted by illness.

Scenario #2

A child with pulmonary disease can have problems in school environments or at night. With current technology, monitoring the health of the child can be difficult. For example, parents talk to the school twice a day to make sure their child is ok because the school "can't tell when he isn't doing well" even though parents say they can tell that he breaths faster, does less activity, has a higher HR and lower oxygen level. Many parents have anxiety about children in other environments (e.g., daycare, school) or at night. In contrast, with (consumer or medical space grade versions) of the present technology, the embodiments of the wearable device can provide appropriate monitoring and reporting thereby decreasing parent/caregiver anxiety in children with chronic illness. The following table illustrates one such example:

| Example - Consumer or medical device: 3 year old with cardiopulmonary disease* on or off oxygen | | | | | | |
|---|---|---|---|---|---|---|
| Activity level* | Rest - well | Walk/ playing - well | Rest - ill | Walk/ playing - ill | Asleep - well | Asleep - ill |
| Steps or distance | | 600 steps | | 200 steps | | |
| HR mean | 100 | 130 | 120 | 160 | 90 | 135 |
| RR mean | 20 | 26 | 25 | 35 | 16 | 22 |
| OX Sat mean | 96% | 94% | 94% | 91% | 91% | 88% |
| Temperature mean | 96.8 F. | 97 F. | 96.8 F. | 97 F. | 96.8 F. | 101 F. |
| Moisture mean | 0 | +1 | +1 | +3 | 0 | +4 |
| Notification | Baseline data calculated | | Parents notified - −10% baseline; interactive questions: check oxygen tank if on oxygen; cold symptoms? | | Baseline | Parents notified - 15% baseline at night need to check child |

Example - Consumer or medical device: 3 year old with cardiopulmonary disease* on or off oxygen

| Activity level* | Rest - well | Walk/ playing - well | Rest - ill | Walk/ playing - ill | Asleep - well | Asleep - ill |
|---|---|---|---|---|---|---|
| Award/feedback | AT baseline parents assured and no need to talk to school | | Child gets more oxygen, treatment given and parents come get child; data transmitted to doctors office | | At baseline parents not anxious and don't need to check child at night | Child gets more oxygen, treatment given and parents come get child; or data transmitted to doctors office |

*Any child with chronic illness will have changes in most of these vital signs from baseline including movement or activity (e.g.: Diabetes low sugar, seizures). The device can be programmed to the child's baseline and variance for notification. This can also work for any adult with cognitive impairment or disabilities. Vital sign monitoring and movement is the essence of health that provide parents or care givers with reassurance.

Scenario #3

Consider an infant or young child admitted with bronchiolitis or asthma. With current technology, the patient state could be improving but the hospital provider is hesitant to discharge as the patient is borderline to discharge without some observation. In contrast, various embodiments of the present technology provide for a (medical grade device) with a wearable that allows for monitoring linked to health care center to allow the patient to be discharged a day early with monitoring at home. It is possible to intervene with treatment if the child begins to worsen and or assure improvement. The following table illustrates an example of such a scenario:

Example - Medical device: 12 month old with bronchiolitis

| Activity level* | Rest awake- hospital sick | Rest asleep- hospital sick | Rest awake- home getting sicker | Rest asleep- home getting sicker | Rest awake- home return to baseline well status | Rest asleep- return to baseline well status |
|---|---|---|---|---|---|---|
| Steps or distance | | | | | | |
| HR mean | 140 | 110 | 150 | 130 | 95 | 100 |
| RR mean | 45 | 38 | 55 | 45 | 28 | 22 |
| OX Sat mean | 93% | 90% | 91% | 88% | 95% | 94% |
| Temperature mean | 96.8 F. | 97 F. | 96.8 F. | 97 F. | 96.8 F. | 97 F. |
| Moisture mean | +1 | +2 | +2 | +4 | +0 | +0 |
| Auditory recording | % crying/ irritability | % crying/ irritability | % increased crying/ irritability | % increased crying/ irritability | % decreased crying/ irritability | % decreased crying/ irritability |
| Notification | Baseline hospital sick data calculated at discharge | | Physician notified - 10% worse from discharge baseline; interactive questions: check oxygen tank if on oxygen;? treatment give? | | Physician notified +30% from hospital sick baseline | |
| Award/feedback | | | Data transmitted to doctors office; treatment provided or directed to return for evaluation | | No contact necessary - see regular physician for follow up as planned. Day of hospital charges saved. | |

Scenario #4

As another example, various embodiments of the present technology may be applied to population management of high risk asthma or other health conditions. In many cases, families or patients are told to monitor some type of action plan for management. (In Asthma treatment, this is called an asthma action plan). In accordance with various embodiments, medical grade devices that interact with a wearable allow for monitoring linked to a health care center and action plan programmed to physiological changes with a clear medication plan included. In scenarios where the physiological changes are extremely off the baseline, then the action plan provides a transition to health care provider. When the patient is a % off baseline a video could be request of the patient—which would show environment and a visual of the patient's condition.

Scenario #5

Pulmonary rehabilitation can increase health status, decrease depression and may be associated with improved outcomes. Patients traditionally have a hard time getting to facilities. Also, a 6 minute walk is a key variable of cardiopulmonary health status. In accordance with some embodiments, a device could be programmed with a rehab program and a health care facility monitors the progress % of baseline of the patient with feedback for motivation or new treatment and could be linked to a group of others for motivation. The 6 minute walk could be programmed and monitored in real life and not in the clinic with % from baseline.

Scenario #6

With current technology, there are no good outcome measures for clinical trials for infant and young children. As a result, it is difficult to tell treatment response. With various embodiments of a medical-grade version of the wearable, sensors can be used to provide short-term and long-term improvement from a % pretreatment baseline.

Exemplary Computer System Overview

Aspects and implementations of the personalized heath care sensor system of the disclosure have been described in the general context of various steps and operations. A variety of these steps and operations may be performed by hardware components or may be embodied in computer-executable instructions, which may be used to cause a general-purpose or special-purpose processor (e.g., in a computer, server, or other computing device) programmed with the instructions to perform the steps or operations. For example, the steps or operations may be performed by a combination of hardware, software, and/or firmware.

Figure 23:
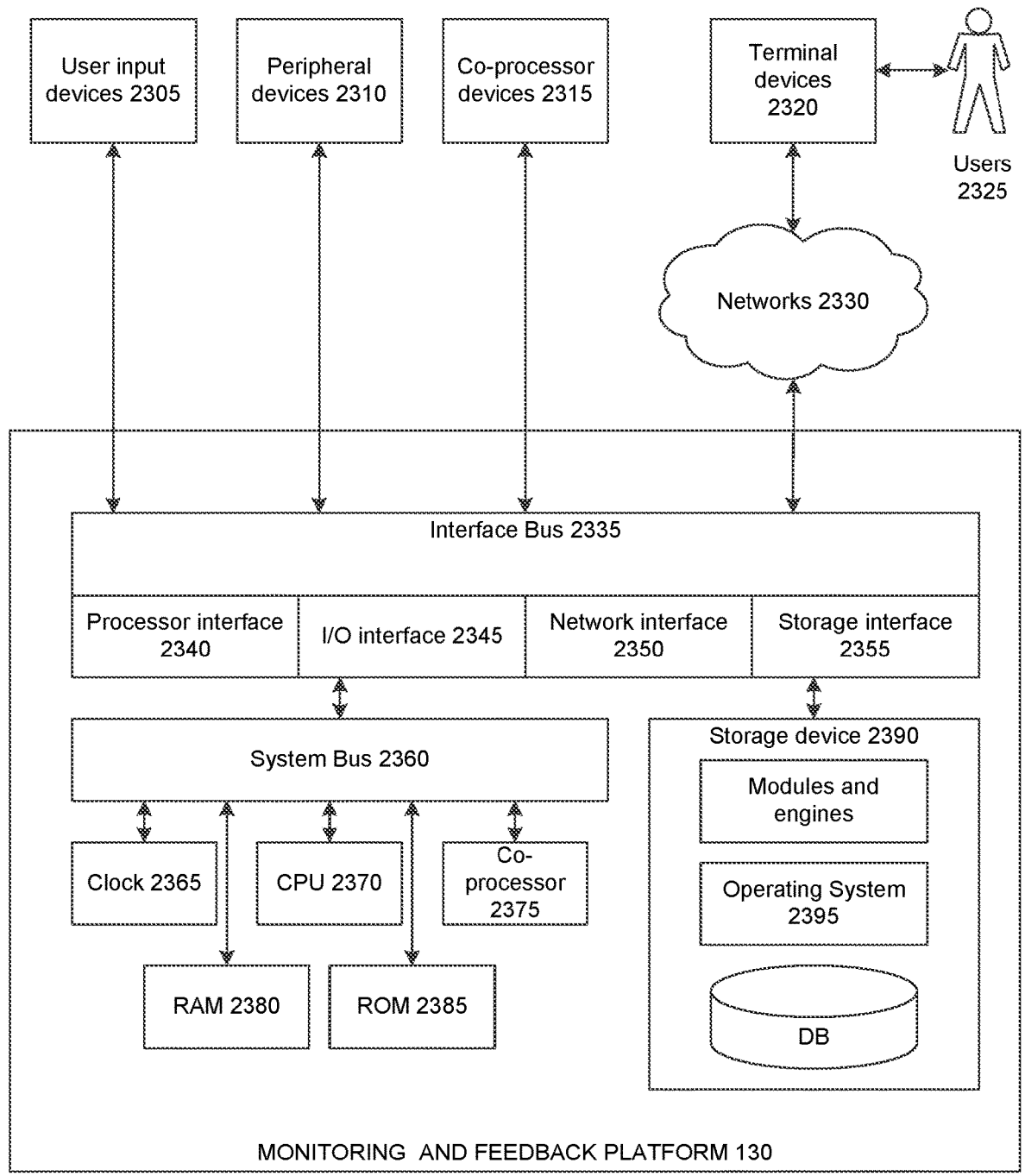
FIG. 23 is a block diagram illustrating an example machine representing the computer systemization of monitoring and feedback platform that may be used in one or more embodiments of the present technology.

FIG. 23 is a block diagram illustrating an example machine representing the computer systemization of monitoring and feedback platform 130. Monitoring platform 130 may be in communication with entities including one or more users 2325 client/terminal devices 2320 (e.g., devices 110A-110N), user input devices 2305, peripheral devices 2310, an optional co-processor device(s) (e.g., cryptographic processor devices) 2315, and networks 2330 (e.g., 120 in FIG. 1). Users may engage with the monitoring and feedback platform 130 via terminal devices 2320 over networks 2330.

Computers may employ central processing unit (CPU) or processor to process information. Processors may include programmable general-purpose or special-purpose microprocessors, programmable controllers, application-specific integrated circuits (ASICs), programmable logic devices (PLDs), embedded components, combination of such devices and the like. Processors execute program components in response to user and/or system-generated requests. One or more of these components may be implemented in software, hardware or both hardware and software. Processors pass instructions (e.g., operational and data instructions) to enable various operations.

Monitoring platform 130 may include clock 2365, CPU 2370, memory such as read only memory (ROM) 2385 and random access memory (RAM) 2380 and co-processor 2375 among others. These monitoring and feedback platform components may be connected to a system bus 2360, and through the system bus 2360 to an interface bus 2335. Further, user input devices 2305, peripheral devices 2310, co-processor devices 2315, and the like, may be connected through the interface bus 2335 to the system bus 2360. The interface bus 2335 may be connected to a number of interface adapters such as processor interface 2340, input output interfaces (I/O) 2345, network interfaces 2350, storage interfaces 2355, and the like.

Processor interface 2340 may facilitate communication between co-processor devices 2315 and co-processor 2375. In one implementation, processor interface 2340 may expedite encryption and decryption of requests or data. Input output interfaces (I/O) 2345 facilitate communication between user input devices 2305, peripheral devices 2310, co-processor devices 2315, and/or the like and components of the monitoring and feedback platform 130 using protocols such as those for handling audio, data, video interface, wireless transceivers, or the like (e.g., Bluetooth, IEEE 1394a-b, serial, universal serial bus (USB), Digital Visual Interface (DVI), 602.11a/b/g/n/x, cellular, etc.). Network interfaces 2350 may be in communication with the network 2330. Through the network 2330, the monitoring and feedback platform 130 may be accessible to remote terminal devices 2320. Network interfaces 2350 may use various wired and wireless connection protocols such as, direct connect, Ethernet, wireless connection such as IEEE 602.11a-x, and the like.

Examples of network 2330 include the Internet, Local Area Network (LAN), Metropolitan Area Network (MAN), a Wide Area Network (WAN), wireless network (e.g., using Wireless Application Protocol WAP), a secured custom connection, and the like. The network interfaces 2350 can include a firewall which can, in some aspects, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including, for example, the access and operation rights of an object by an individual, a machine, and/or an application, and the circumstances under which the permission rights stand. Other network security functions performed or included in the functions of the firewall, can be, for example, but are not limited to, intrusion-prevention, intrusion detection, next-generation firewall, personal firewall, etc., without deviating from the novel art of this disclosure.

Storage interfaces 2355 may be in communication with a number of storage devices such as, storage devices 2390, removable disc devices, and the like. The storage interfaces 2355 may use various connection protocols such as Serial Advanced Technology Attachment (SATA), IEEE 1394, Ethernet, Universal Serial Bus (USB), and the like.

User input devices 2305 and peripheral devices 2310 may be connected to I/O interface 2345 and potentially other interfaces, buses and/or components. User input devices 2305 may include card readers, finger print readers, joysticks, keyboards, microphones, mouse, remote controls, retina readers, touch screens, sensors, and/or the like. Peripheral devices 2310 may include antenna, audio devices (e.g., microphone, speakers, etc.), cameras, external processors, communication devices, radio frequency identifiers (RFIDs), scanners, printers, storage devices, transceivers, and/or the like. Co-processor devices 2315 may be connected to the monitoring and feedback platform 130 through interface bus 2335, and may include microcontrollers, processors, interfaces or other devices.

Computer executable instructions and data may be stored in memory (e.g., registers, cache memory, random access memory, flash, etc.) which is accessible by processors. These stored instruction codes (e.g., programs) may engage the processor components, motherboard and/or other system components to perform desired operations. The monitoring and feedback platform 130 may employ various forms of memory including on-chip CPU memory (e.g., registers), RAM 2380, ROM 2385, and storage devices 2390. Storage devices 2390 may employ any number of tangible, non-transitory storage devices or systems such as fixed or removable magnetic disk drive, an optical drive, solid state memory devices and other processor-readable storage media. Computer-executable instructions stored in the memory may include the monitoring and feedback platform 130 having one or more program modules such as routines, programs, objects, components, data structures, and so on that perform particular tasks or implement particular abstract data types. For example, the memory may contain operating system (OS) component 2395, modules and other components, database tables, and the like. These modules/components may be stored and accessed from the storage devices, including from external storage devices accessible through an interface bus.

The database components can store programs executed by the processor to process the stored data. The database components may be implemented in the form of a database that is relational, scalable and secure. Examples of such database include DB2, MySQL, Oracle, Sybase, and the like. Alternatively, the database may be implemented using various standard data-structures, such as an array, hash, list, stack, structured text file (e.g., XML), table, and/or the like. Such data-structures may be stored in memory and/or in structured files.

The monitoring and feedback platform 130 may be implemented in distributed computing environments, where tasks or modules are performed by remote processing devices, which are linked through a communications network, such as a Local Area Network ("LAN"), Wide Area Network ("WAN"), the Internet, and the like. In a distributed computing environment, program modules or subroutines may be located in both local and remote memory storage devices. Distributed computing may be employed to load balance and/or aggregate resources for processing. Alternatively, aspects of the monitoring and feedback platform 130 may be distributed electronically over the Internet or over other networks (including wireless networks). Those skilled in the relevant art(s) will recognize that portions of the system may reside on a server computer, while corresponding portions reside on a client computer. Data structures and transmission of data particular to aspects of the monitoring and feedback platform 130 are also encompassed within the scope of the disclosure.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A monitoring and feedback platform comprising:
a processor;
a database containing a plurality of baseline profiles,
wherein each of said plurality of baseline profiles indexed to a physiological parameter;
a communications component configured to receive a set of physiological data collected from a wearable monitoring device including a network of sensors capable of measuring one or more physiological parameters including respiration rate and blood oxygen level;
an evaluation module configured to:
identify said measured physiological parameters;
retrieve from said database one of said plurality of baseline profiles based on said measured physiological parameters;
apply one or more machine learning algorithms to said set of physiological data;
compare said set of physiological data of said measured physiological parameters to said baseline profile retrieved from said database; and
generate a health status by comparing said measured physiological parameters to said baseline profile retrieved from said database,
wherein said health status comprises a pediatric asthma score based on said measured physiological parameters, and
wherein said measured physiological parameters comprise respiratory rate and pulse oximetry.

2. The monitoring and feedback platform of claim 1, wherein the evaluation module generates an alert sent to a monitoring device when said health status falls below a threshold, said threshold automatically set by said evaluation module based on nonnative variation in said baseline profile.

3. The monitoring and feedback platform of claim 1, further comprising an analysis engine to aggregate baseline profiles from multiple users and a machine learning algorithm applied to identify key variables that would change the health status.

4. The monitoring and feedback platform of claim 1, wherein said measured physiological parameter further includes one or more of: heart rate, body moisture, and body temperature.

5. The monitoring and feedback platform of claim 4, collecting environmental data including one more of: environmental particulate data, ambient air temperature data, and geospatial location data.

6. The monitoring and feedback platform of claim 1, wherein said predicted pediatric asthma score based on said measured physiological parameters of respiration rate and blood oxygen level and by applying said machine learning algorithm, as follows:

$$f = \frac{\sum_{i=1}^{6} w_i f_i}{\sum_{i=1}^{6} w_i}$$

wherein $f = w_1 f_1 + w_2 f_2$ $w_1 = \mu_1(p_1) * \mu_1(p_2)$ $w_2 = \mu_2(p_1) * \mu_2(p_2)$ and wherein each of the input data measurements has membership weight value (wi) calculated:

$$w_i = \prod_{j=1} \mu(Pj)$$

wherein $\mu(p_1)$ comprises a membership function, wherein:
$p_1$ is the measurement value of RR, wherein RR is input 1 (in1)
$p_2$ is the measurement value of SpO2, wherein SpO2 is input 2 (in2), and wherein:

If $p_1$ is in1cluster1 and SpO2 is in2cluster1, then
$f_1 = \mu_1(p_1)p_1 + \mu_1(p_2)p_2 + r_1$ If $p_1$ is in1cluster2 and SpO2 is in2cluster2, then
$f_2 = \mu_2(p_1)p_1 + \mu_2(p_2)p_2 + r_2$ wherein $\mu_1(p_1)$ is the membership function of input p1 or input 1 in said cluster 1; and
wherein $\mu_2(p_1)$ is the membership function of input p1 or input 1 in said cluster 2.

7. The monitoring and feedback platform of claim 1, wherein said predicted pediatric asthma score based on said measured physiological parameters comprising: blood oxygen level, fraction of inspired oxygen, heart rate, and respiratory rate, and wherein each of said physiological parameters includes a plurality of data measurements having a membership in one of a plurality of clusters, and wherein the machine learning algorithm is applied to the data measurements based on membership within said plurality of clusters to obtain a final output, as follows:

$$f = \frac{\sum_{i=1}^{6} w_i f_i}{\sum_{i=1}^{6} w_i}$$

and wherein each of the input data measurements each have a membership weight value (wi) calculated:

$$w_i = \prod_{j=1}^{6} \mu_i(p_j).$$

8. A monitoring and feedback platform, comprising:
a processor;
a database containing a plurality of baseline profiles,
wherein each of said plurality of baseline profiles indexed to a physiological parameter;
a communications component configured to:
collect environmental data from an external monitoring station, wherein said environmental data includes concentration of oxygen in the air;
collect a set of physiological data from a wearable monitoring device including a network of sensors capable of measuring one or more physiological parameters including respiration rate, blood oxygen level, and fraction of inspired oxygen;
an evaluation module configured to:
identify measured physiological parameters, wherein said measured physiological parameters comprise respiration rate and blood oxygen level based on said physiological data collected from said wearable monitoring device, and fraction of inspired oxygen based on the said environmental data collected from said external monitoring station;

retrieve from said database one of said plurality of baseline profiles based on said measured physiological parameters;

apply one or more machine learning algorithms to said set of physiological data;

compare said set of physiological data of said one or more measured physiological parameters to said baseline profile retrieved from said database; and generate a health status by comparing said measured physiological parameters to said baseline profile retrieved from said database.

9. The monitoring and feedback platform of claim 8, wherein health status comprises a predicted pediatric asthma score.

10. The monitoring and feedback platform of claim 9, wherein said predicted pediatric asthma score based on said measured physiological parameters of respiration rate and blood oxygen level and by applying said machine learning algorithm, as follows:

$$f = \frac{\sum_{i=1}^{6} w_i f_i}{\sum_{i=1}^{6} w_i}$$

wherein $f = w_1 f_1 + w_2 f_2$ $w_1 = \mu_1(p_1) * \mu_1(p_2)$ $w_2 = \mu_2(p_1) * \mu_2(p_2)$ and wherein each of the input data measurements has membership weight value (w calculated:

$$w_i = \prod_{j=1} \mu(Pj)$$

wherein $\mu(p_j)$ comprises a membership function, wherein:

$p_1$ is the measurement value of RR, wherein RR is input 1 (in1)

$p_2$ is the measurement value of SpO2, wherein SpO2 is input 2 (in2), and wherein:

If $p_1$ is in1cluster1 and SpO2 is in2cluster1, then
$f_1 = \mu_1(p_1)p_1 + \mu_1(p_2)p_2 + r_1$ If $p_1$ is in1cluster2 and SpO2 is in2cluster2, then
$f_2 = \mu_2(p_1)p_1 + \mu_2(p_2)p_2 + r_2$ wherein $\mu_1(p_1)$ is the membership function of input p1 or input 1 in said cluster 1; and wherein $\mu_2(p_1)$ is the membership function of input p1 or input 1 in said cluster 2.

11. The monitoring and feedback platform of claim 9, wherein said predicted pediatric asthma score based on said measured physiological parameters comprising: blood oxygen level, fraction of inspired oxygen, heart rate, and respiratory rate, and wherein each of said physiological parameters includes a plurality of data measurements having a membership in one of a plurality of clusters, and wherein the machine learning algorithm is applied to the data measurements based on membership within said plurality of clusters to obtain a final output, as follows:

$$f = \frac{\sum_{i=1}^{6} w_i f_i}{\sum_{i=1}^{6} w_i}$$

and wherein each of the input data measurements each have a membership weight value (wi) calculated:

$$w_i = \prod_{j=1}^{6} \mu_i(p_j).$$

* * * * *